United States Patent [19]

Hill et al.

[11] Patent Number: 5,098,711
[45] Date of Patent: * Mar. 24, 1992

[54] METHOD OF TREATING THE ORAL CAVITY WITH DENTAL FLOSS CONTAINING CHEMOTHERAPEUTIC AGENTS

[76] Inventors: Ira Hill, Clay Ct., Locust, N.J. 07760; Robert D. White, 65 Glen Gray Rd., Oakland, N.J. 07436

[*] Notice: The portion of the term of this patent subsequent to Mar. 27, 2007 has been disclaimed.

[21] Appl. No.: 452,829

[22] Filed: Dec. 20, 1989

Related U.S. Application Data

[63] Continuation-in-part of Ser. No. 270,161, Nov. 14, 1988, abandoned, and a continuation-in-part of Ser. No. 270,162, Nov. 14, 1988, abandoned, and a continuation-in-part of Ser. No. 270,164, Nov. 14, 1988, abandoned, and a continuation-in-part of Ser. No. 270,166, Nov. 14, 1988, abandoned, and a continuation-in-part of Ser. No. 270,353, Nov. 14, 1988, abandoned, and a continuation-in-part of Ser. No. 270,562, Nov. 14, 1988, Pat. No. 4,911,927.

[51] Int. Cl.⁵ ............................................. A61K 7/16
[52] U.S. Cl. .............................. 424/401; 424/49; 132/321; 132/323; 433/216; 433/217.1
[58] Field of Search .......................... 132/321-329; 433/215, 216, 217.1; 424/49-58, 401

[56] References Cited

U.S. PATENT DOCUMENTS

| | | | |
|---|---|---|---|
| 872,908 | 12/1907 | Cutter | 132/323 |
| 1,069,874 | 8/1913 | Hansom | 132/329 |
| 1,149,376 | 8/1915 | Leonard et al. | 132/323 |
| 1,936,456 | 11/1933 | Larson et al. | 167/68 |
| 2,004,957 | 6/1935 | Messner | 167/82 |
| 2,024,146 | 12/1935 | Crowther | 167/93 |
| 2,027,535 | 1/1936 | Jacobson | 167/93 |
| 2,031,233 | 2/1936 | Stillwell | 167/82 |
| 2,035,267 | 3/1936 | Fleischman | 167/93 |
| 2,054,742 | 9/1936 | Elbel | 167/93 |
| 2,069,157 | 1/1937 | Sahyun | 167/93 |
| 2,089,845 | 8/1937 | Atkins | 167/93 |
| 2,124,971 | 7/1938 | Eisenberg et al. | 167/93 |
| 2,154,168 | 4/1939 | Klein et al. | 167/93 |
| 2,381,142 | 8/1945 | Stonehill | 132/321 |
| 2,667,443 | 1/1954 | Ashton | 433/216 |
| 2,677,700 | 5/1954 | Jackson et al. | 260/488 |
| 2,748,781 | 6/1956 | Collat | 132/325 |
| 2,778,045 | 1/1957 | Bly et al. | 15/131 |
| 2,896,639 | 7/1959 | Fleming | 132/321 |
| 3,164,524 | 1/1965 | Fand et al. | 167/93 |
| 3,228,845 | 1/1966 | Najjar | 167/93 |
| 3,427,380 | 2/1969 | Kirkland | 424/54 |
| 3,427,381 | 2/1969 | Kirkland | 424/54 |
| 3,431,339 | 4/1969 | Gyarmathy et al. | 424/52 |
| 3,475,533 | 5/1966 | Mayrand | 424/57 |
| 3,574,824 | 4/1971 | Echeandia et al. | 424/50 |
| 3,574,943 | 4/1971 | Stark et al. | 433/217.1 |
| 3,629,468 | 12/1971 | Anderson | 424/44 |
| 3,639,563 | 2/1972 | Januszewski | 424/49 |
| 3,651,207 | 3/1972 | Lauster et al. | 424/50 |
| 3,699,979 | 10/1972 | Muhler et al. | 132/321 |
| 3,729,553 | 4/1973 | Gold et al. | 424/44 |
| 3,772,431 | 11/1973 | Mikvy et al. | 424/44 |
| 3,830,246 | 8/1974 | Gillings | 132/89 |
| 3,838,702 | 10/1974 | Standish et al. | 132/321 |
| 3,864,472 | 2/1975 | Pensak et al. | 424/54 |
| 3,887,701 | 6/1975 | Nachtigal | 424/54 |
| 3,888,976 | 6/1975 | Mikvy et al. | 424/44 |
| 3,897,795 | 8/1975 | Engel | 132/321 |
| 3,897,796 | 8/1975 | Erickson | 132/321 |
| 3,907,991 | 9/1975 | Accetta | 424/130 |
| 3,929,988 | 12/1975 | Barth | 424/54 |
| 3,942,539 | 3/1976 | Corliss et al. | 132/79 |
| 3,943,949 | 3/1976 | Ashton et al. | 132/321 |
| 3,947,570 | 3/1976 | Pensak et al. | 424/54 |
| 3,957,964 | 5/1976 | Grimm, III | 424/10 |
| 4,029,113 | 6/1977 | Guyton | 132/321 |
| 4,034,771 | 7/1977 | Guyton | 132/91 |
| 4,069,312 | 1/1978 | Mannara | 424/49 |
| 4,071,614 | 1/1978 | Grimm, III | 424/49 |
| 4,082,841 | 4/1978 | Pader | 424/50 |
| 4,100,269 | 7/1978 | Pader | 424/49 |
| 4,130,636 | 12/1978 | Tomlinson | 424/52 |
| 4,170,633 | 10/1979 | Wagenknect | 424/48 |
| 4,414,990 | 11/1983 | Yost | 132/321 |
| 4,476,107 | 10/1984 | Schmolka | 424/49 |
| 4,511,563 | 4/1985 | Schmolka | 514/162 |
| 4,548,219 | 10/1985 | Newman et al. | 132/91 |
| 4,554,154 | 11/1985 | White | 424/16 |
| 4,610,871 | 9/1986 | Lynch | 424/48 |
| 4,611,309 | 3/1977 | Lutz | 424/49 |
| 4,638,823 | 1/1987 | Newman et al. | 132/321 |
| 4,673,354 | 6/1987 | Culler | 433/217.1 |
| 4,911,927 | 3/1990 | Hill et al. | 132/323 |

FOREIGN PATENT DOCUMENTS

| | | | |
|---|---|---|---|
| 0086440 | 8/1983 | European Pat. Off. | |
| 0335466 | 10/1989 | European Pat. Off. | 132/321 |
| 2832005 | 2/1979 | Fed. Rep. of Germany | 132/321 |
| 55-90555 | 7/1980 | Japan | 433/216 |
| 58-120782 | 7/1983 | Japan | 433/216 |
| 1262857 | 10/1989 | Japan | 132/321 |
| 2128133 | 4/1984 | United Kingdom | |

OTHER PUBLICATIONS

J. Afseth et al., Caries Res. 17: 472-475 (1983).
G. Bowden, J Canad Dent Assn, No. 2, 1984.
G. Harrap et al., Archs Oral Biol., vol. 29, No. 2, pp. 87-91 (1984).
G. Harrap et al., Journal of Periodontal Research (1983) 18:634-642.
R. Havenaar, J. Dent. Res. Feb. 1984, vol. 63, No. 2, pp. 120-123.

(List continued on next page.)

*Primary Examiner*—Shep K. Rose
*Attorney, Agent, or Firm*—Ernest V. Linek

[57] ABSTRACT

Disclosed is a method of treating the oral cavity with a surfactant, silicone, and chemotherapeutic agent containing preparation released from dental floss to alter local microbial ecology including: plaque formation, gingivitis and *S. mutans* count.

13 Claims, No Drawings

OTHER PUBLICATIONS

W. Loesche et al., JADA, vol. 106, Apr. 1984, pp. 587–592.

K. Makinen et al., JADA, vol. 111, No. 1985, pp. 745–751.

J. Mordenti et al., Journal of Pharmaceutical Sciences, vol. 71, No. 12, Dec. 1982.

R. Segal et al., Journal of Pharmaceutical Sciences, vol. 74, No. 1, Jan. 1985.

Southard et al., Jada, vol. 108, Mar. 1984.

Topitsoglou et al., Caries Res. 17:369–378 (1983).

Winter et al., Caries Res. 16:349–352 (1982).

Plaque: Current Approaches to Prevention and Control; JADA, vol. 109, Nov. 1984.

Fine et al., Journal of Clinical Periodontology, 12: 660–666 (1985).

J. Van Houte, Reviews of Infectious Diseases, vol. 5, Supplement 4, Sep.–Oct. (1983).

Baker et al., J. Periodontal Res. 13: 474–485, (1978).

Tanzer et al., Antimicrobial Agents and Chemotherapy, vol. 15, No. 3, 408–414 (1979).

C. Baker, Dent. Items of Interest, 70: 921–934 (1948).

Keene et al., Jada, vol. 93, 328–333 (1976).

Lobene et al., Clinical Preventive Dentistry, vol. 4, No. 1, 5–8 (1982).

Finkelstein et al., J. Dent. Res., vol. 58, No. 3, 1034–1039, (1979).

Wright et al., Clinical Preventive Dentistry, vol. 1, No. 3, (1979).

Wright et al., J. Dent. Res., vol. 56, No. 6, (1977).

Van Swol et al., Military Medicine, 391–394 (1977).

Horowitz et al., J. Den. Res., 56: 1977 Spec. Iss. A.

METHOD OF TREATING THE ORAL CAVITY WITH DENTAL FLOSS CONTAINING CHEMOTHERAPEUTIC AGENTS

CROSS-REFERENCE TO RELATED APPLICATIONS

The following U.S. Patent Applications are related to the invention described and claimed herein:

Ira Hill & Robert White Ser. No. 06/927,805 Filed: Nov. 6, 1986 METHOD OF INTERRUPTING THE FORMATION OF PLAQUE now, U.S. Pat. No. 4,950,479;

Ira Hill & Robert White Ser. No. 06/927,752 Filed: Nov. 6, 1986 DENTAL AND ORAL HYGIENE PREPARATIONS; now allowed;

Ira Hill & Robert White Ser. No. 07/270,165 Filed: Nov. 14, 1988 DENTAL STIMULATOR now, U.S. Pat. No. 4,942,034;

Ira Hill & Robert White Ser. No. 07/270,544 Filed: Nov. 14, 1988 DENTAL FLOSS now, abandoned;

Ira Hill & Robert White Ser. No. 07/453,302 Filed: Dec. 20, 1989 DENTAL FLOSS WITH CHEMOTHERAPEUTIC AGENTS now, pending;

Ira Hill & Robert White Ser. No. 07/270,562 Filed: Nov. 14, 1988 METHOD AND APPARATUS FOR ADDING CHEMOTHERAPEUTIC AGENTS TO DENTAL FLOSS now, U.S. Pat. No. 4,911,927;

Ira Hill & Robert White Ser. No. 07/270,162 Filed: Nov. 14, 1988 METHOD OF TREATING THE ORAL CAVITY WITH DENTAL FLOSS now, abandoned;

Ira Hill & Robert White Ser. No. 07/270,163 Filed: Nov. 14, 1988 DENTAL FLOSS WITH TETRACYCLINE now, abandoned;

Ira Hill & Robert White Ser. No. 07/270,723 Filed: Nov. 14, 1988 DENTAL FLOSS WITH STABILIZED STANNOUS FLUORIDE now, abandoned;

Ira Hill & Robert White Ser. No. 07/270,132 Filed: Nov. 14, 1988 DENTAL FLOSS WITH CHLORHEXIDINE now, abandoned;

Ira Hill & Robert White Ser. No. 07/270,167 Filed: Nov. 14, 1988 DENTAL FLOSS WITH SODIUM FLUORIDE now, abandoned;

Ira Hill & Robert White Ser. No. 07/270,135 Filed: Nov. 14, 1988 DENTAL FLOSS WITH POLYVINYL PYROLLIDONE COMPLEX OF IODINE now, abandoned;

Ira Hill & Robert White Ser. No. 07/270,161 Filed: Nov. 14, 1988 METHOD OF TREATING THE ORAL CAVITY WITH DENTAL FLOSS CONTAINING TETRACYCLINE now, abandoned;

Ira Hill & Robert White Ser. No. 07/270,353 Filed: Nov. 14, 1988 METHOD OF TREATING THE ORAL CAVITY WITH DENTAL FLOSS WITH STANNOUS FLUORIDE now, abandoned;

Ira Hill & Robert White Ser. No. 07/270,166 Filed: Nov. 14, 1988 METHOD OF TREATING THE ORAL CAVITY WITH DENTAL FLOSS WITH CHLORHEXIDINE now, abandoned;

Ira Hill & Robert White Ser. No. 07/270,164 Filed: Nov. 14, 1988 METHOD OF TREATING THE ORAL CAVITY WITH DENTAL FLOSS CONTAINING POLYVINYL PYROLLIDONE IODINE COMPLEX now, abandoned;

Ira Hill & Robert White Ser. No. 07/324,894 Filed: Mar. 17, 1989 ALCOHOL-FREE PRE-RINSE EMULSIONS now, pending;

Ira Hill & Robert White Ser. No. 07/325,216 Filed: Mar. 17, 1989 METHOD OF TREATING THE ORAL CAVITY now, pending;

Ira Hill & Robert White Ser. No. 07/326,179 Filed: Mar. 17, 1989 METHOD OF MANUFACTURING AN ALCOHOL FREE PRE-RINSE EMULSION now, pending.

This application is a continuation-in-part of the following copending applications:

(1) Ser. No. 07/270,161—Filed Nov. 14, 1988, entitled Method of Treating the Oral Cavity with Dental Floss Containing Tetracycline, now abandoned;

(2) Ser. No. 07/270,162—Filed Nov. 14, 1988, entitled Method of Treating the, Oral Cavity with Dental Floss, now abandoned;

(3) Ser. No. 07/270,164—Filed Nov. 14, 1988, entitled Method of Treating the Oral Cavity with Dental Floss Containing Polyvinyl Pyrollidone Iodine Complex, now abandoned;

(4) Ser. No. 07/270,166—Filed Nov. 14, 1988, entitled Method of Treating the Oral Cavity with Dental Floss with Chlorhexidine, now abandoned;

(5) Ser. No. 07/270,353—Filed Nov. 14, 1988, entitled Method of Treating the Oral Cavity with Dental Floss with Stannous Fluoride, now abandoned; and (6) Ser. No. 07/270,562—Filed Nov. 14, 1988, entitled Method and Apparatus for Adding Chemotherapeutic Agents to Dental Floss, now U.S. Pat. No. 4,911,927; the disclosures of which are hereby incorporated herein by reference.

FIELD OF THE INVENTION

The present invention relates to oral hygiene and specifically to a method of treating the oral cavity with an innovative interproximal delivery system comprising a dental floss with improved cleaning, conditioning and antimicrobial properties, the floss further containing chemotherapeutic agents, e.g., antimicrobials, antibiotics, antioxidants, desensitizers, and anti-tartar agents, such as tetracycline, chlorhexidine, sodium fluoride, stannous fluoride, and polyvinyl pyrollidone iodine complex with iodine.

BACKGROUND OF THE INVENTION

Proper use of dental floss is necessary to clean the considerable area on the interproximal surfaces of teeth, which cannot be reached by the bristles of a toothbrush. The purpose of dental floss is:

1. to dislodge and remove any decomposing food material that has accumulated at the interproximal surfaces that cannot be removed by brushing, and
2. to dislodge and remove as much as possible the growth of bacterial material (plaque) upon the teeth or the superimposed calculus that has accumulated there since the previous cleaning.

The concept of the use of dental floss for cleansing interproximal spaces appears to have been introduced by Parmly in 1819 ["Practical Guide to the Management of the Teeth," Collins & Croft, Philadelphia Pa]. Parmly suggested the use of waxed silk to clean teeth of persons subject to gingival inflammation. Numerous types of floss were developed and used for cleaning, until finally in 1948 Bass established the optimum characteristics of dental floss. (*Dental Items of Interest*, 70, 921-34, (1948)).

Surprisingly, floss marketers have ignored Bass for the past 40 years. Bass warned that dental floss treated with sizing, binders and/or wax produces a "cord" effect which reduces flossing efficiency dramatically. Almost all floss sold today including unwaxed floss contains binders and/or sizing substances. These "sticky" substances are used to keep the floss twists from unwinding during use and to keep the floss turns from falling off a spool during dispensing by holding the floss together.

Additionally, most floss sold at retail today is also "waxed" to assist penetration to interproximal regions; as the "cord" effect described by Bass makes the floss bundle difficult to force between closely spaced teeth.

The optimum characteristics of dental floss as described by Bass in 1948 are ignored by today's flosses. Specifically, Bass suggests that these waxed and sized flosses produce the "cord" effect discussed above as distinguished from the "spread effect" of unwaxed, unsized floss which flattens out and widens, with the filaments spread out. The potential for separate mechanical action of spread out filaments is nullified by this "cord" effect, as are the spaces between the filaments, which according to Bass are necessary to receive, hold and remove the microscopic material dislodged during flossing. Thus, the mechanical cleaning attributed to spread filaments and essentially all of the evacuation of microscopic materials from the interproximal spaces by entrapment is impaired or sacrificed with waxed and/or sized flosses, because of this "cord" effect.

As an alternative to sizing, binders, wax etc., Bass suggests "steamset" to set the twist in dental floss so that the floss will not untwist during use. Commercial floss twisters and floss spoolers, opted to use various binders and sizing materials instead. These "sticky" substances facilitate floss handling, keep the floss from untwisting during use, and keep the floss from falling off the spool. Although steamset floss does not untwist during use, absent sticky substances, it does unravel off the spool during dispensing and during spooling. Thus, the optimum floss described by Bass could not be manufactured commercially in 1948, so apparently, water insoluble binders, sizing and wax were adopted early on and continue up to the present.

From 1960 thru 1962, numerous clinical studies reported that there is no clinical difference as to plaque removal and gingivitis scores between waxed and unwaxed dental floss. Note, both are "cord" flosses and contain sizing, binders etc. These studies also confirmed that waxed and unwaxed floss are approximately 50% effective with respect to plaque removal and gingivitis scores. Thus the "cord" effect severely restricts efficiency of flossing.

O'Leary in 1970, and Hill et al. in 1973, found no difference in the interproximal cleansing properties of waxed or unwaxed dental floss. This was reconfirmed in 1982 by Lobene et al. [*Clinical Preventative Dentistry*, Jan-Feb] who showed no significant clinical difference on plaque and gingivitis scores. Similar results, i.e., no clinical difference between waxed and unwaxed floss with respect to reduced gingival inflammation were shown by Finkelstein in 1979 [*J. Dent. Res.*, 58: 1034-1039]. No differences in gingival health were shown by Wunderlich in 1981 [*J. Dent. Res.*, 60A: 862]. No differences in plaque removal were reported by Schmidt et al. in 1962 [*J. Dent. Res.*] with flosses of various types. Stevens in 1980, studied floss with variable diameters and showed no difference in plaque and gingival health. Carter et al., *Va Dent. J.*, 52: 18-27 (1975), studied professional and self-administered waxed and unwaxed floss, both significantly reduced gingival bleeding of interproximal and gingival sulci. Unwaxed floss appeared slightly, but not significantly more effective.

In view of this clinical work, it is not surprising that most of the dental floss sold today is bonded and/or waxed. The "bonding" in the yarn industry today is used more to facilitate processing and production during floss manufacture and packaging than for "flossing" reasons. Since clinical tests show no difference between waxed and unwaxed floss (both unfortunately are "bonded") the floss industry has been comfortable with the yarn industry's propensity to use bonding agents in floss.

Today there are three basic nylon strand constructions approved by the FDA for flossing. These are 140 denier (68 filament), 100 denier (34 filament), and 70 denier (34 filament). Analysis of the commercial flosses sold worldwide show that almost all flosses available are twisted in generally the same manner, contain bonding agents, and are constructed by twisting several (6-10) strands selected from one of these three strand types.

Almost 100% of the floss sold today is manufactured by "yarn" manufacturers with little consideration given to the influence of twisting of floss construction on cleaning, etc.

The simple removal of binders, to allow the floss strands to spread out, introduces a "user-unfriendly" effect which reduces the value Bass described. Commercial flosses with little or no binders are notorious for frustrating flossers with their tendency to fray, break etc. The removal of binders requires adjunct (lubricants, etc.) to reduce snagging, fraying, etc.

In view of the foregoing, it is not surprising that shred resistant floss has been the basic claim of some floss marketers. The most recent introduction of a Goretex type floss, with its monofilament construction, should prove to to the ultimate shred resistant floss. Historically, the typical response to shredding was to develop a "tighter" bonded and smaller diameter floss that did not spread out and did not shred. Waxing was also an option. It is not difficult to see how the "ultimate cord", i.e., monofilament construction, evolved from this approach. The monofilament floss is reported to be easier to use than traditional bonded flosses.

Somehow it has become generally accepted throughout the oral care community today that:
1. the daily mechanical disruption and removal of dental plaque with a standard bonded dental floss is a very effective method of interproximal plaque control, and
2. it would be difficult to demonstrate clinical superiority over the standard commercial flosses.

This conclusion contradicts the mediocre plaque and gingivitis control effect of standard floss as reported consistently in the literature, to wit:
1. The literature has repeatedly documented that gingivitis scores flattened after 4 weeks of flossing with scores routinely in the 60's. See Lobene et al. and other waxed v. unwaxed dental floss studies.
2. Many researchers report that the best floss in the hands of experts will only remove 50 to 60% of the interproximal plaque.
3. Keene in 1976 [J. Am. Dent. Assoc., 93: August], reported that ". . . ordinary waxed dental floss was neither an efficient debriding agent nor an effective tool for delivery of the test agents to the interproximal sites", and 4. Additionally, Finkelstein and Grossman, supra, Hill et al., supra, Carter et al., [*J. Periodont.*, 44: 411–413 (1973)], Wunderlich et al., supra, Schmid et al., *J. Dent. Res.*, 60A: 122 (1981), Lamberts et al., and Stevens, each showed plaque reductions and/or improved gingitivity or improved gingival health with flossing. These results were comparable to Lobene et al., i.e., that floss was 50% to 60% effective, and thus traditional floss leaves room for substantial improvement.

There is, therefore a definite need in the art for an improved dental floss, to clean, condition and treat the surfaces flossed.

SUMMARY OF THE INVENTION

Proper flossing procedure as recently described in "Dental Health Adviser" includes: "slide it (floss) between your teeth using a gentle sawing action" and "scrape the sides of your teeth with an up and down motion".

The present invention is based upon the discovery that this type of mechanical action can be supplemented by the release of surfactants from the floss into the interproximal region. These released surfactants are readily solubilized in saliva and interproximal fluids to produce a detersive effect in the interproximal region during flossing. Foaming of the surfactant is avoided by the use of silicone conditioners, thus optimizing this detersive effect.

Thus, the present invention may be broadly defined as a method of treating the oral cavity for the improved removal of plaque, through the use of an interproximal delivery system comprising a unique dental floss, said floss containing a cleaning preparation comprising a surfactant and a coating substance at from between 5 and about 100% by weight of the weight of the floss strands, and optionally further containing up to about 50% by weight of an active chemotherapeutic agent selected from the group consisting of antimicrobials, antibiotics, antioxidants, desensitizers, and anti-tartar agents.

The surface active properties of the surfactant and silicone presented interproximally, not only assist in cleaning debris and plaque from the interproximal sites, and condition teeth and gums but they also alter the surface tension of the plaque remaining; as well as disrupting plaque matrix reattachment.

The preferred dental flosses useful in the present method of treating the oral cavity are described in the following copending applications:

(1) Ser. No. 07/270,132—Filed Nov. 14, 1988, entitled Dental Floss with Chlorhexidine, now abandoned;
(2) Ser. No. 07/270,135—filed Nov. 14, 1988, entitled Dental Floss with Polyvinyl Pyrollidone Complex of Iodine, now abandoned;
(3) Ser. No. 07/270,163—Filed Nov. 14, 1988, entitled Dental Floss with Tetracycline, now abandoned;
(4) Ser. No. 07/270,167—Filed Nov. 14, 1988, entitled Dental Floss with Sodium Fluoride, now abandoned;
(5) Ser. No. 07/270,544—Filed Nov. 14, 1988, entitled Dental Floss, now abandoned; and
(6) Ser. No. 07/270,723—filed Nov. 14, 1988, entitled Dental Floss with Stabilized Stannous Fluoride, now abandoned;

the disclosures of which are hereby incorporated herein by reference.

This improved lifting of debris, plaque and soil from the interproximal spaces with surfactants is further enhanced by the use of unbonded floss strands which spread out and follow the contours of the teeth during flossing/cleaning. This improved mechanical cleaning is further supplemented with various insoluble abrasives released interproximally from the floss during flossing. This combination of abrasive, surfactant and mechanical action is more efficient than mechanical action alone with waxed floss.

The floss of the present invention may be more appropriately described as a local delivery system, suitable for the topical cleaning and/or treatment of those hard-to-reach areas between teeth (interproximal spaces) and the areas immediately below the gumline (i.e., the gingival crevice).

The unique construction of the floss and loading of cleaners, active ingredients and conditioners in the space around each of the nylon fibers allows loading of these substances from 10 to over 100% by weight of the floss. The "loaded" floss tends to "splay" (open up), when pressure is applied to the floss, i.e., the pressure required to fit the floss between teeth and/or, after the floss is positioned between teeth, the pressure applied during flossing. When the floss is splayed, the loaded substances are released and continue to be released during the sawing motion of flossing. This releasing action supplements the cleaning action of flossing by releasing cleaners to work with the floss.

In a preferred embodiment, the present invention may be defined as the treatment of the oral cavity with an interproximal delivery system comprising:

a. floss having from between two and 12 strands, each containing between about 100 and 800 filaments with a denier between 300 and about 1200, and b. a cleaning preparation at from between 5 and about 100% by weight of said strands, wherein:
  i. said filaments are substantially free from sizing and binding agents;
  ii. said interproximal delivery system splays upon being worked between interproximal surfaces;
  iii. said interproximal delivery system release from between about 10 and about 80% by weight of said cleaning preparation upon splaying; and
  iv. said cleaning preparation:
    a. is loaded into said delivery system as a substantially aqueous free, hot-melt emulsion,
    b. is contained throughout the interproximal delivery system, primarily in the area surrounding said filaments with less than about 5% by weight of said cleaning preparation on the outermost surface of said delivery system, and c. can contain up to about 50% by weight of an active chemotherapeutic agent selected from the group consisting of: antimicrobials, antibiotics, antioxidants, desensitizers, and anti-tartar agents.

The following features of the present invention characterize the surfactant/silicone/abrasive enhancement effect produced when flossing interproximally:

1. Rapid release of substantial quantities of saliva soluble surfactant, silicone and abrasive when the floss is pulled across tooth surfaces. The construction of the floss, the use of unbonded floss, the absence of wax and a unique loading process which encourages the floss to open up and release the load during flossing.

2. Rapid solubilization of a surfactant with high detergency, and saliva solubility, combined with simethicone produce excellent detersive results with no foaming, and 3. The tendency to use "fresh" loaded floss is for each interproximal site flossed. The addition of hedonic substances, flavor oils, silicone, "mouth-feel" affecting gums, etc. to the load encourage the flosser to unwind fresh floss prior to flossing a new site. Thus, the flosser is hedonically driven to use fresh floss with the present invention.

The potential development of hedonically superior flosses has been surprisingly restricted and may be a critical factor in the failure of flossing and may be a critical factor in the failure of flossing to penetrate more than about 10% of the adult U.S. market.

The superior flavored flosses available commercially are based on "encapsulated flavor" technology where the flavors are delivered in a spray dried matrix form to the bonded floss. See U.S. Pat. No. 3,943,949, the disclosure of which is hereby incorporated herein by reference. These flavored flosses are available waxed or unwaxed. Less effective application application and retention of flavor is also commercially achieved by direct contact of the floss with flavor oil/solvent solutions. The inherent limitations of the encapsulated flavored flosses are evident when these products are compared to "flavor oil in a solidified melt emulsion" treated flosses of the present invention.

Other hedonic areas critical to a positive consumer response towards flossing such as "mouth feel" have not been addressed by current floss products.

It is generally accepted that floss is not a "user-friendly" product, i.e., it is difficult to do. It causes pain and bleeding and it results in a bad taste in the mouth. Most market researchers agree that anything that can be done to make flossing more positive should be implemented to encourage more frequent flossing and more wide spread floss use. The addition to floss of: full spectrum flavor oils, mouth conditioning substances such as silicones, and cleaners and abrasives that leave a "clean, just brushed feeling" as taught by the present invention, are all sources of positive feed back to the flosser that would be considered encouraging and supportive. To achieve these requires basic changes in floss construction, physical chemistry of floss additives and new "loading" technology that goes beyond waxing and the "yarn" (cord) approach to floss construction.

With the advent of "loading active ingredients" into floss for release during flossing as discussed below, the opportunity is available to include desensitizing agents into the load to minimize flossing pain and discomfort. Typically, desensitizing agents such as strontium chloride are used in dentifrices for "sensitive" teeth. These substances produce a comparable effect when released interproximally from the floss of the present invention. This desensitizing effect further improves the overall hedonics of the floss of the present invention. Examples of floss of the present invention with desensitizers as an added chemotherapeutic agent are described below.

Analysis of current waxed floss users shows a consistent tendency to "re-use the floss" and not to use a fresh piece of floss for each interproximal site. The spent "waxed" floss, under close inspection shows little entrapped, dislodged microscopic particle because of the "cord" effect.

In contrast, as noted above users of the floss of the present invention show a consistent tendency to use "fresh" floss for each new interproximal region. Additionally, the "spent" floss of the present invention contains entrapped substances which can be observed by the flosser. This tends to motivate the use of fresh floss as well. The mouth feel and taste imparted by the floss reinforces that the floss is working by leaving a clean, fresh feeling in the mouth.

Surprisingly, when the chemotherapeutic agents of the present invention are added to floss strands they perform one critical function of the standard size or binder in that they keep the floss from untwisting during use and impart the "stickiness" necessary to allow the floss to be spooled and dispensed without unraveling. However, because of the chemistry of these substances and the loading process used; contrary to the bonded or waxed floss, the loaded floss of the present invention spreads out during use to obtain the separate mechanical action of the many filaments.

This spreading out during flossing, also triggers the release mechanism which discharges most of the load interproximally during flossing, i.e., up to about 80% by weight. The surfactant/silicone/abrasive mixture thus, released is readily solubilized in the saliva and other fluids present. This solubilized mixture responds to the separate mechanical action of the floss filaments resulting in a nonfoaming detersive effect in the interproximal space.

Release of the load leaves spaces in the floss which tend to take up and hold some of the microscopic substances dislodged during flossing. These "captured" substances can be easily observed in the "spent" floss.

The floss of the present invention is preferably a nylon dental floss that has been processed to load into it up to about 80 mg/yd of the cleaning and plaque fighting formulation described in copending application Ser. No. 06/927,752, filed Nov. 6, 1986, entitled "Dental and Oral Hygiene Preparations," the disclosure of which is hereby incorporated herein by reference.

Up to about 80% of this load is released onto interproximal and subgingival sites during flossing, i.e., up to about 64 mg/yd. This release of surfactant cleansing in the area flossed is not available with flosses sold today. The flosses of the present invention show superior cleaning over waxed or unwaxed commercial flosses.

Additionally, the floss of the present invention can contain therapeutic substances for release at concentrations up to 40 mg/yd. When these substances are included in the load they are released onto those interproximal and subgingival sites which cannot be reached by rinsing or brushing. This interproximal release of substances in these concentrations is unique, in that it improves plaque control and gingivitis scores over other dental flosses.

Most authorities agree that the control of periodontal diseases requires:
1. regular disruption of subgingival microflora, and
2. regular removal of supergingival plaque.

Many rinses and dentifrices claim supragingival control of plaque and/or tartar. None are proved effective subgingivally and have limited supragingival effect interproximally. Floss has been proven to have some subgingival mechanical disruption value, but no chemotherapeutic value subgingivally or supergingivally.

In contrast, regular flossing with the floss of the present invention provides a unique combination of mechanical action, detersive action, surface modification and chemotherapy which results in:
a. disruption of subgingival microflora, and
b. removal of interproximal supragingival plaque.

Subgingival chemotherapeutic disruption of microflora is achieved by the unique combination of:
a. chemical cleansing with surfactants released form the floss of the present invention,
b. prolonged modification of the surface chemistry of the microflora by the coating materials released, e.g., silicones, released from the floss, and
c. alteration of microflora with various active ingredients contained in the load and released during flossing.

Subgingival mechanical disruption of microflora is achieved by the unique combination of:
a physical disruption by the "spread-out", lubricated floss fibers,
b. abrasive, disruption with abrasives released from floss including: silica, dicalcium phosphate, pyrophosphates etc., at concentrations up to 40 mg/yd; and
c surfactant disruption resulting from the release of surfactants during flossing.

Chemotherapeutic removal of supergingival plaque is achieved by the unique combination of:
a. chemical cleansing with surfactants released from the floss,
b. modification of the surface chemistry of the plaque with coating materials e.g., silicones, and
c. alteration of the plaque with various active ingredients contained in the load and released during flossing including: tetrasodium pyrophosphate, tetrapotassium pyrophosphate etc.

Mechanical removal of supragingival plaque is achieved by the unique combination of:
a physical removal by the unbonded, spread out, lubricated floss fibers,
b. abrasive removal by the abrasives released from the floss including: silica,dicalcium phosphate, pyrophosphates etc., and
c. cleansing resulting from the release of surfactants during flossing.

Plaque is a microbially formed coating on tooth surfaces, bound together by natural polymers, (mucopolysaccharides) formed by a microbial action on salivary fluids, cell debris, food remnants, sugars and starches in the mouth. Embedded in this polymer matrix are the bacteria normal to the oral cavity but, when rapped against tooth surfaces and protected by the matrix from easy removal, are in excellent position for "mischief". Most dental texts implicate plaque in the formulation of caries, or tooth decay. In addition, these embedded bacteria release toxins that cause gingivitis, bleeding and swelling of the gums. Gingivitis can lead to periodontitis in which gums recede, pockets of infection form and teeth loosen.

Plaque formation is an ongoing process. Various gel and paste dentifrice preparations, mouth rinse and mouth prerinse preparations, make plaque and/or tartar control claims. One disadvantage of these preparations is that only a relatively short time during which the teeth are being cleaned or the mouth is being rinsed is available for these preparations to take effect. These preparations generally have little residual effect on plaque formation. Further these rinses are limited to supragingival plaque and tartar control and have little access to the critical interproximal area. In contrast, the floss of the present invention releases substances interproximally and subgingivally. Additionally, some of these preparations such as mouth rinses and prerinses contain various antimicrobial substances which may alter the critically balanced microflora of the mouth. Generally, these substances are introduced into the oral cavity in large quantities due to the dilute nature of the delivery vehicle.

Effective oral hygiene requires that three control elements be maintained by the individual:
1. Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.
2 Surfactant Cleansing. This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, health mouth.
3. Frequency of Cleansing. This is perhaps the most difficult to provide in today's fast-paced work and social environment. Most people recognize that their teeth should be brushed at least 3 times a day and flossed at least once a day. The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Most surprising, less than 10% of adults floss regularly. Reasons offered for not flossing; difficult to do, painful, not effective and leaves a bad taste. Overall, floss is not a "consumer friendly" product.

Since plaque is regarded by most of the dental profession as a causative agent leading to various dental pathologies discussed in detail below, there is considerable desire by most consumers to remove or prevent the formation of plaque on a daily basis.

There are four oral care techniques which address the problem of plaque: abrasion, antimicrobial agents, removal of precursors to plaque, and altering the attachment of plaque to a surface.
1. Abrasive removal of the plaque film, once it has firmly adhered to the tooth surface, is the only totally effective cleansing mechanism. Again, professional dental hygiene is most effective, but recently, a number of special abrasive toothpastes have been accepted by dental organizations for partially removing supragingival adhered plaque and the tartar which subsequently forms from the plaque. Heretofore, interproximal plaque could only be removed by mechanical means such as flossing and/or by use of appropriately shaped dental stimulators. Dental stimulators containing the substances of the present invention are disclosed in copending application Ser. No. 07/270,165 Nov. 14, 1988, entitled "Dental Stimulator," U.S. Pat. No. 4,942,034 the disclosure of which is hereby incorporated herein by reference.

2. Antimicrobial action can affect plaque formation in two ways, (a) reducing the number of bacteria in the mouth which form the mucopolysaccharides and (b) killing those bacteria trapped in the film to prevent further growth and metabolism. However, the medical and dental community is divided about the advisability of frequent use of antimicrobial agents in the mouth in rinses or prerinses, especially the most effective ones, except under strict supervision of licensed practitioners. There are a number of reasons given, but one concern is that such materials would upset the ecological balance of the mouth. A balanced, "friendly" microbial population is necessary to prevent pathogenic organisms from taking over.

By contrast, delivery of antimicrobial agents directly to the critical sites would more effectively treat the disease or pre-disease condition with localized concentrations. The microflora of these sites could be altered with appropriate substantive antimicrobials. Obviously, a more effective cleansing and physical removal, such as provided by the present invention, reduces even further the required total concentrations of antimicrobials required to produce efficacy.

3. Removal of plaque precursors requires the reduction of food sources and building blocks required for the bacteria to synthesize the mucopolysaccharides which polymerize into the plaque film. Going far back into the chain of evens leading to plaque formation and interrupting the chain has much to commend it as a sound oral hygiene strategy. However, for this technique to be effective, the plaque building blocks must be interrupted periodically throughout the mouth, especially at the site of plaque buildup and if possible just below the tooth-gum interface and interproximally. Such disruption is copending applications Ser. Nos. 927,752, now allowed and 927,805, now U.S. Pat. No. 4,958,479 filed Nov. 7, 1986, the disclosures of which are hereby incorporated herein by reference. Most other oral hygiene preparations described above fall short on "frequency-of-use" basis, abrasion and cleaning. For reference see, L. Menaker, "The Biologic Basis of Dental Caries", Chapters, 5, 11, 12, 14, 16 and 18, Harper and Row (1980).

4. As to altering attachment of plaque, it has now been found that the cleaning and coating compositions described below can be incorporated into dental floss of specified construction at surprisingly high concentrations; considering that the compositions of the present invention are not soluble in the floss. Secondly, floss so treated will "release" these compositions during flossing and chemically cleanse the area of plaque and plaque precursors, bacteria, etc., while coating teeth and gum surfaces with a plaque matrix disrupting substance. The release of these substances is particularly effective in disrupting, for prolonged periods, the plaque matrix on these interproximal sites. The cleaning that results from the compositions released from the floss also takes place on those interproximal surfaces brushing does not reach. This chemical cleansing and matrix disruption adds a new dimension to flossing beyond the physical removal of debris from these surfaces.

DETAILED DESCRIPTION OF THE PREFERRED EMBODIMENTS

The floss used in the method of the present invention comprises:

a. multi strand dental floss containing, an ingestible, nonfoaming, plaque disrupting composition comprising cleaners and coating substances dispersible in said cleaners wherein:
  a. the multi-strand floss:
    1. contains from between 2 and 12 strands,
    2. has a denier between about 300 and about 12,000, and
    3. contains between about 100 and about 800 filaments;
  b. the strands include natural and/or synthetic fibers and mixtures thereof including cotton, silk, polyester and nylon;

In a preferred embodiment of the present invention the floss used is nylon, contains between 4 and 8 strands, with a denier between about 500 and 1000 and contains between about 200 and 600 filaments. In a particularly preferred embodiment of the present invention the floss used is nylon, containing 6 strands, has a denier of about 840 and has approximately 408 filaments.

c. the cleaners include: surfactants and emulsifiers such as:
sodium lauryl sulfate,
sodium lauroyl sarcosinate,
polyethyleneglycol stearate,
polyethyleneglycol monostearate,
coconut monoglyceride sulfonates,
soap powder,
sodium alkyl sulfoacetates,
alkyl polyglycol ether carboxylates such as those described in U.S. Pat. No. 4,130,636;[1]
polyoxyethylene derivatives of sorbitan esters, such as those described in U.S. Pat. Nos. 3,639,563[1]; 3,947,570,[1]
propoxylated cetyl alcohol as described in U.S. Pat. No. 2,677,700[1]; and

[1]—each hereby incorporated herein by reference.

Preferred commercially available substances which include:
polyoxyethylene, polyoxybutylene block copolymers such as Pluronic F108, and F127 (BASF) and polysorbates such as Tween 40, and 80, (Hercules).

Particularly preferred surfactants include block copolymers comprising a cogeneric mixture of conjugated polyoxybutylene and polyoxyethylene compounds having as a hydrophobe, a polyoxybutylene polymer of at least 1200 molecular weight; such as described in U.S. Pat. Nos. 4,343,785, 4,465,663, 4,511,563 and 4,476,107,[2] and

[2]—each hereby incorporated herein by reference.

d. the coating substances can be characterized as follows, they:
    1. suppress the tendency of the surfactant cleaners that are present to foam,
    2. are safely ingestible at the concentrations used,
    3. have an affinity for mouth and teeth surfaces,
    4. are neutral, inert and do not support biological activity,
    5. modify the surface energy properties of oral cavity surfaces such that it is more difficult for food particles, cellular debris and various plaque precursors and formers to attach to these oral cavity surfaces,
    6. form a fugitive thin, transparent coating that does not build up on oral cavity surfaces and is removed by the normal clearing and flushing action of the mouth,
    7. impart a pleasant "smooth" feeling to the surfaces of the mouth, gums and teeth, and 8. retain various flavors, sweeteners and pharmacologically preparations active on surfaces of the mouth imparting an unexpected prolonged effect of the pharmacologically active substances as well as prolonged flavor perception, and
9. The preferred coating substances include:
   various silicones,
   carbowaxes,
   polymers such as: silicone glycol copolymers, polydimethyl siloxanes,
   long chain hydrocarbons, especially normal paraffins having a chain length of 16 carbon atoms or greater, paraffins with several loci of branching and unsaturation, where the extent of such branching and unsaturation does not create unacceptable toxicity nor lower the solidification point below body temperature,
   and polymers which have limited solubility in ethanol and water solutions where the ethanol; water ratio is greater than 0.3:1 but have essentially no solubility in water or saliva at lower ratios.

The combination of these cleaners with these coating substances, wherein the latter is inherently insoluble in the former, in a treated dental floss is novel. The prolonged plaque matrix disruption so obtained with a floss containing this combination in the mouth, is novel.

Furthermore, the cleaner, coating substance, and saliva or gingival crevice fluid mixture obtained when the compositions are released in the mouth are ingestible and can be pleasantly swallowed, which further distinguishes it from typical oral cleaning compositions used with a toothbrush and most rinses and prerinses. For example, unlike typical cleaners used in dentifrice pastes, the cleaners of the preferred floss do not fill the mouth with foam and can be pleasantly swallowed which is necessary for those flosses loaded with substantial quantities of releasable materials.

The compositions released from the floss during flossing can disrupt plaque formation without resort to antimicrobial ingredients. The various surfaces of teeth and gums are coated with a smooth thin film released from the floss which disrupts plaque formation. These coatings remain in the interdontal spaces for extended periods and prolong this disruption effect on plaque matrix formation.

Alternatively, for those embodiments of the present invention where specific localized antimicrobial ingredients are therapeutically desirable, these compositions provide an excellent carrier. Thus, the floss may additionally comprise one or more chemotherapeutic agents, for example, tetracycline, chlorhexidine, sodium fluoride, stannous fluoride, and/or polyvinyl pyrollidine iodine complex, to mention but a few. Given the teachings of this disclosure, the skilled artisan will readily be able to supplement this list of chemotherapeutic agents with those desired for any particular application.

A review of the construction of the preferred floss used in the method of the present invention shows that the compositions employed are contained essentially in the interstitial spaces between the fibers of the floss with minimum composition on the outer surface of the floss. This internal loading of the compositions is achieved by opening up the floss fibers during manufacturing and introducing a melt-emulsion of the compositions of the preferred floss into the space around the opened fibers.

The preferred floss used in the method of the present invention is unique in its capacity to release the "loaded" compositions interproximally. Unexpectedly, the property of releasing these compositions correlates with the opening up and/or flattening of the treated floss strands during flossing. This tendency of the preferred loaded floss to open up and flatten out during flossing allows the floss fibers:
   a. to pass easily between teeth which are so closely spaced as to make insertion of typical floss difficult and painful,
   b. to conform to the surface of the teeth,
   c. to fit under the gum line at the gingival margin, and
   d. to slip into subgingival areas in order to dislodge plaque bacteria, microflora etc. Historically, plaque, bacteria, pathogenic bacterial plaque etc., collect around the gum line and in various shallow pockets that form in this area. The subgingival plaque, bacteria, microflora etc., requires regular disruption to control periodontal diseases.

As discussed above, floss has generally been waxed or bonded to reduce shredding. Such treatment results in the floss tending to hold its shape during flossing which results in the floss generally not flattening out, with less than optimum conformation to teeth surfaces and interproximal surfaces. Thus, it is difficult to reach those remote interproximal areas without risk of pain and/or damaging delicate gum tissue. In contrast, the preferred loaded floss used in the method of the present invention, opens up tends to conform to surfaces and releases the loaded substances interproximally during flossing. This release mechanism results in:
1. the floss strands which are lubricated flattening to reduce shredding and minimize stripping of the load prior to reaching the interproximal sites;
2. the floss stands flattening and conforming to the surfaces over which they are worked and reaching most remote interproximal surfaces;
3. the floss strands continuing to release the loaded substances during flossing as the floss is moved over teeth, under the gum line and over the interproximal surfaces; and
4. the floss being easier to manipulate over the interproximal sites and near the gingival margin of the teeth where meticulous oral hygiene has been impaired heretofore. These are historically the most bleeding prone areas of the mouth because heretofore they have been the most difficult to keep plaque free.
5. Finally, the flattening, conforming and lubricating properties of the floss of this invention makes it much more pleasant to use, replacing the frequently experienced pain and bleeding attendant with use of ordinary floss with a hedonically positive experience.

Thus, the release mechanism of the preferred floss allows the floss to reach the interproximal sites and physically remove plaque, while at the same time releasing the compositions contained therein interproximally to assist in cleaning and/or treating these interproximal sites. This releasing of the compositions was quantified as follows:

Floss described in Example 39 of Table IV containing 40 mg of load/yd was cut into 10, one yard lengths. The floss sections were dried at 104 F for two hours and weighed. Unloaded floss was similarly heated and weighed. Two individuals flossed with five pieces each of the treated floss and with the unloaded floss. Both types of floss were again dried at 104 F for two hours and reweighed. The average quantity of loaded active ingredients released was established at 26 mg/yd with no significant variation between individuals or between pieces of floss.

The "load" of the compositions on the preferred floss into the interstitial spaces between floss fibers also provides a suitable vehicle for effectively delivering other therapeutic substances to the interproximal sites. The load can include very small quantities (say 100 units per yard in the case of very active antibiotics) to large amounts (up to 60% by weight of anti-tartar or other chemicals requiring mass action) across a wide variety of therapeutic substances. Thus, chemotherapeutic treatment of interproximal sites can also be achieved.

For example, specific bacterial diseases in the oral cavity can be more effectively treated if various antibiotics can be introduced topically to specific interproximal sites. These include: penicillin, polymyxin B, vancomycin, kanamycin, erythromycin, niddamycin, metronidazole, and spiramycin which can be included in the compositions on the preferred floss and loaded into a chemotherapeutic floss of the present invention. Tetracycline is one preferred antibiotic agent in the floss employed in the method of the present invention.

The topical application of various antibiotics to interproximal sites as well as subgingivally is preferred over "systemic" treatments with these substances. That is, the risk of adverse side reactions to the patient which accompanies most ingested systemic antimicrobials is reduced substantially. In addition, application of the antimicrobial to specific infected areas can be achieved with a higher frequency, topically than systemically. This assures higher antibiotic concentrations at the site(s) of infection and a higher incidence of effectiveness in a shorter period of time. See Goodson Implant references 1979 to 1988.

Additionally, various chemical agents can be added to the floss as anti-plaque/anti-gingivitis agents including:
a. anti-plaque and anti-tartar substances such as the tetrasodium or tetrapotassium pyrophosphates and zinc chloride,
b. first generation agents which are antibacterial agents with limited substantivity such as oxygenating compounds, quaternary ammonium compound, phenolic compounds and plant alkaloids such as sanguinarine, and
c. second generation agents which are antibacterial agents with substantivity such as chlorhexidine, either free base or as the gluconate or other suitable salt, alexidine, octenidine and stannous fluoride. The treatment of the oral cavity with stannous fluoride and chlorhexidine antimicrobials in the preferred flosses are preferred embodiments of the present invention.

The use of loaded floss containing various antimicrobial substances offers the opportunity to disrupt subgingival microflora and limit regrowth while also controlling supragingival plaque. The release interproximally and subgingivally of substantive chemotherapeutic antimicrobials and the plaque disrupting compositions from the preferred floss tends to:
a. disrupt or eliminate supragingival plaque, and pathogenic subgingival flora, and
b. alter the environment interproximally and subgingivally sufficiently to prevent regrowth of disease associated microorganisms. The resulting control of plaque quantity and the periodontopathic microorganisms in plaque should help control gingivitis.

The first generation agents suitable for use in the method of the present invention include:
1. quaternary ammonium compounds such as benzethonium chloride, cetylpyridinium chloride,
2. phenolic compounds such as thymol and eucalyptol in a mixture of methyl salicylate, benzoic acid and boric acid and phenol,
3. natural extracts (flavor oils) known to possess antimicrobial properties, and
4. sanguinarine extract, alone or in combination with zinc chloride, or zinc chloride along.

It is suggested that the preferred floss used herein containing these anti-plaque and anti-gingivitis agents provides an important adjunct to the prevention and control of gingivitis when used with regular personal oral hygiene procedures and professional care.

Surprisingly, the cleaning/coating compositions released during the practice of the present invention retain good surface active properties and are able to clear the interproximal areas of some cell debris, food debris, material alba, sugars, starches and other precursors to plaque. This cleaning is obtained with minimal foaming while simultaneously coating the interproximal surfaces with a thin neutral film containing the flavorants of the compositions. This neutral film is not metabolizable by resident oral cavity microorganisms.

By contrast, natural film formers such as lecithin-containing substances and fats are known to form anti-attachment films on mouth surfaces but these films are not suitable for the purposes of the present invention since they are metabolizable and are not neutral. Most of these naturally occurring coating substances support biological activity rather than form non-supportive inert films and as such, work opposite of the suitable film formers of the present invention. See for example: Menaker, "The Biologic Basis of Dental Caries", Chapter 16: Gibbons and Hoote, *Ann. Rev. of Microbiol.*, 29, pp. 19–44; and Hayes, *J. Dent. Res.*, 632, pp. 2–5 (1984).

As long as this transient inert coating of the present invention remains, it:
1. restricts the subsequent adherence of plaque forming materials to the teeth, thus continuing the disruption of plaque formation:
2. continues to impart a "smooth" feeling to the mouth, and
3. prolongs the flavor perception after flossing.

These features are described in various Examples below. The prolonged flavor perception, described as a "clean, brushed feeling" between the teeth, is particularly novel and unexpected and makes flossing a more pleasant experience.

Most users of the floss of the present invention perceive a quite different feeling in the mouth than is perceived with typical flosses. For example,
1. The treated floss slides comfortably between teeth producing less pain, especially between "tight" teeth, and desensitizing agents reduce discomfort normally encountered with sensitive or bleeding gums.
2. The treated floss releases the compositions contained therein/thereon onto surfaces of teeth and gums more effectively cleaning the interproximal sites.
3. The released compositions condition teeth and gums and leave the mouth feeling exceptionally clean and smooth. The surfaces of the teeth are smoother and shiny. The prolonged flavor perception is generally described as "freshness" and is stronger, more natural tasting and persists much longer with the released compositions than when state-of-the-art, encapsulated "flavored" flosses are used under comparable conditions.

Frequency of cleansing is encouraged by the unique characteristics of the present invention. These cause the user to return to the present invention regularly, stimulated as much by the pleasant experiences as by conscious recall of "my mouth needs flossing". These characteristics are: the product is exceptionally pleasant to use.

The various flavors and conditioners in the composition of the preferred floss are formulated to be as pleasant as a good quality candy mint and to contribute this pleasant taste over a longer-than-expected time period thus enhancing the "its working" perception without negative "dirty mouth" connotations due to the bad taste of released plaque and debris. The latter is found to reduce frequency of use and undermine the regular cleansing advantage.

The feeling in the mouth is equally pleasant. A smooth, tingly "something's happening" feeling is perceived immediately upon flossing, followed by a clean, fresh, well lubricated mouth and teeth surfaces which unexpectedly persist much longer than mints, gums, breath fresheners and even mouth washes and toothpastes. Surprisingly, the inner teeth surfaces adjacent to gum tissue also feel clean and fresh—a phenomena perceived by most consumers only after gently prophylaxis by a dentist.

Research shows that it is not unreasonable for a typical user of the instant floss to use about 18 inches/use and to carry the dispenser in pocket or purse for use after snacks or meals.

The higher flavor levels which can be pleasantly incorporated into the preferred floss, contribute to the plaque controlling properties of this invention. For example, natural and synthetic flavor and sweetener agents as diverse as menthol, xylitol and glycyrrhizin are known to be beneficial towards plaque control and are included in the compositions of this invention. See, for example, Segal, *J. Pharm. Sci.*, 74:79–81 (1985) and Makkinen, *J. Am. Dent. Assoc.*, 111:740–741 (1985).

In addition to the cleaning and/or coating composition described above, preferred embodiments of the present invention use various viscosity control agents to impart certain viscosity characteristics to the products used in the present invention. It is believed that in these preferred embodiments of the present invention, viscosity plays a role in achieving optimum mouth feel and flavor retention characteristics of the present invention.

Viscosity control agents which are known in the food and consumer products, and not commonly used in floss, can be selected from natural and synthetic gums such as: carragenan, gum tragacanth, methyl cellulose and derivatives there of such as hydroxyethyl methyl cellulose, polyvinyl pyrrolidone, and hydrophilic carboxyvinyl polymers such as those sold under the trademark Carbopol 934.

Generally, about 0.01 percent to about 10 percent of one or more viscosity control agents is used, see Table I. Often these substances are used as dry powders directly incorporated as a third phase into the melt-emulsion mixture. With appropriate control of the active water content, some or all of these dry viscosity agents could be substituted with pre-gelled viscosofiers containing no free water.

In addition to the cleaning and coating compositions described above, a preferred embodiment of the floss used in the present invention includes various solid, insoluble, particulates to:

1. further control viscosity of the melt-emulsion during manufacturing,
2. modify the solid texture of the completed product,
3. impart beneficial and pleasant mouth feel properties to the product which are perceived during use, and
4. optimize cleaning.

These particulates include approximately sized calcium carbonate, talc, silica and dicalcium phosphate. These are described in Table IV below. Most of these are used as dental abrasives. In addition to these abrasives other particulates imparting beneficial properties include salts which are generally insoluble in the compositions of the preferred floss, such as tetra sodium pyrophosphate, tetra potassium pyrophosphate and sodium bicarbonate.

In addition to the stabilizers, viscosity particulates, flavoring and pH buffering ingredients; the compositions of the preferred floss can optionally contain at least one humectant selected from the group consisting of glycerine, xylitol, sorbitol, hydrogenated glucose syrup and propylene glycol. Generally, such humectants are utilized in the proportion of about 0.1 percent to about 25 percent by weight based upon the total weight of the composition. Preferably, the humectant is utilized in an amount of about 3 to 15 percent by weight, see Example below.

Flavors, colorants, sweeteners, non-carcinogenic sugars and humectants are also used to impart optimum cosmetic characteristics to the compositions of the preferred floss.

Generally, the flavoring component is present as an oil, emulsified into the composition by the surfactant component.

The conventional flavoring components are exemplified by the following materials, menthol, anise oil, benzaldehyde, bitter almond oil, camphor, cedar leaf oil, cinnamic aldehyde, cinnamon oil, citronella oil, clove oil, eucalyptol, heliotropine, lavender oil, mustard oil, peppermint oil, phenyl salicylate, pine oil, pine needle oil, rosemary oil, sassafras oil, spearmint oil, thyme oil, thymol, wintergreen oil, lemon and orange oils, vanillin, spice extracts and other flavoring oils generally regarded as safe (GRAS) by health authorities.

Additional adjuvants can be added to provide color, flavor, or sweetening effects, as desired. Examples of suitable sweetening agents include sorbitol, sodium cyclamate, saccharine, commercial materials, such as Nutrasweet brand of aspartame and xylitol. Citric acid or acetic acid is often utilized as a flavor additive. All types of flavoring materials are generally used in amounts of about 1.0 to about 20 percent by weight, preferably about 2.0 percent to about 15 percent by weight.

A buffering ingredient may also be added to the compositions on the preferred floss in order to prevent natural degradation of the flavoring components or therapeutically active ingredients. Generally, the pH of these compositions is adjusted from about 3.5 to about 8, depending on the chemistry of the active ingredient most requiring protection. The buffering ingredients such an alkali metal salt of a weak organic acid, for instance, sodium benzoate, sodium citrate, sodium phosphate, sodium bicarbonate or potassium tartrate is generally added in an amount of about 0.1 to about 1.0 percent by weight. Other buffering agents such as weak organic acids or salts of weak bass and strong acids such as boric acid, citric acid, ammonium chloride, etc., can also be used in similar concentrations.

Stabilizers are often added to the compositions for additional control, such as:

a. sodium benzoate, sodium or potassium sorbate, methyl paraben, propylparaben and others approved for ingestion.
b. chemical oxidative control substances, such as ethylenediamine tetraacetic acid, BHA, BHT, propyl gallate and similar substances approved for ingestion. Concentration levels of these stabilizers comply with industry and regulatory standards.

Successful loading of the composition on the preferred multi-strand dental floss requires unique manufacturing processes other than those presently used to "wax" or "flavor" commercial flosses. For example, processes used for the addition of microencapsulated flavor substances, "flavor oils" or wax to floss do not provide for the quantity of load required for the present invention nor the "controlled release" of this loaded material interproximally during flossing. Those processes used for waxing, for example, primarily coat the outer surfaces of the bundle of floss strands.

In contrast, the compositions on the preferred floss are loaded inside the floss in concentrations ranging from about 10% to about 100% by weight of the floss. This translates to from between about 10 mg and about 100 mg per yard of floss. These loaded substances are then controllably released into the oral cavity during flossing at from between about 10 and about 80% of the load. For example, a floss containing 40 mg/yd of load will release between about 20 and about 32 mg of load during flossing. Note, the rate of release of these loaded active ingredients is easily controlled by varying the floss construction, the process of loading, and the composition of the loaded material, providing additional novelty and utility in the method of the the present invention.

It is critical for the purpose of the method of the present invention that much of this "loading" be accomplished in the interstitial spaces of the floss as distinguished from simply "coating" the outer surfaces of the bundle of floss strands. Much of what is called "Impregnation" in prior floss art is, upon careful examination, primarily "coating". Thus, the pressures and forces encountered during flossing allow for the loaded material to be progressively released interproximally between the teeth and under the gum line. This "interstitial loading" is particularly critical in order to avoid "stripping" the floss of active ingredients while the floss is being inserted between the teeth and to avoid transferring major quantities of loaded materials to the fingers during flossing.

As the floss is worked through the contact point and moved gently under the gumline the loaded substances in the preferred floss are continually released into those areas where plaque and debris are difficult to clean and where irritation bleeding and bacterial infection tend to occur.

In addition to interstitial loading a "secondary dusting" of the surface of the treated floss may be desired. This post addition of dry powder effects the "hand" of the loaded floss and makes some floss easier to hold onto during flossing. The post added compositions include abrasives etc., which can contribute to the efficacy of the floss. These substances are generally added at the rate of between about 0.08 mg and about 9.0 mg per yard of floss and preferably between about 1.0 mg and about 2.0 mg per 1 yard of floss.

Unexpectedly, the construction of dental floss, that is the method used to twist the fibers into the finished floss, has been observed to influence the amount of the compositions in the preferred floss that can be loaded into the interstitial spaces around the fibers. For example in Table I, different floss constructions are described which show variations in load of up to about 400%. In Examples A-E the composition and the method of loading were held constant while the floss construction was varied. Specifically the composition described as Example 39 in Table IV was loaded into the various flosses by the method described in copending application Ser. No. 07/270,562 filed Nov. 14, 1988, now U.S. Pat. No. 4,911,927.

TABLE I

| EXAMPLE | FLOSS CONSTRUCTION (all ends 140/68) | TWIST/INCH | LOAD IN MG/ 25 yds OF F |
|---|---|---|---|
| A | One blue and twisted around prepared by simultaneously twisting two pairs of two white ends previously twisted with one white single end. | 2 | 250 |
| B | Three white ends previously twisted at 1 twist/inch combined with two white and one blue end previously twisted at one twist/inc. | 2 | 500 |
| C | One blue end around a core of two white ends twisted with blue end under lower tension. this in turn twisted around a core of three white previously twisted a core of three white previously twisted. The wrap around (blue containing) twist again under lower tension. | 2 | 1750 |
| D | Three ends twisted simultaneously. Each end comprised of two green ends previously twisted. Post drying left thread "fluffy" with many broken filaments. | 1½ | 1000 |
| E | Two ends twisted; each comprised of three white ends previously twisted at | 1½ | 600 |

TABLE I-continued

| EXAMPLE | FLOSS CONSTRUCTION (all ends 140/68) | TWIST/INCH | LOAD IN MG/ 25 yds OF F |
|---|---|---|---|
| | 1½ twist per inch | | |

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

In Examples 1 thru 4 various compositions were loaded into flosses of various construction and chemical makeup. The loading was done by dipping the floss into an agitated bath containing these compositions. The loaded floss was then hung in the air until cool and tested. The results are discussed in Table II below. Note, in all of these examples the surfactant used was PLURONIC F127, the coating composition, Dow Corning Silicone 1500, the flavor IFF 101. There was no subsequent powder treatment of the floss in these examples.

floss with the post added powder was then tested. Note in all these Examples the surfactant used was Pluronic F 127, the coating composition Dow Corning Silicone 1500, the Flavor IFF 101. Carrageenan was included in the loading composition in all examples. The results are set out in Table III below.

TABLE III

| | LOADING COMPOSITION | | | | | |
|---|---|---|---|---|---|---|
| EXAMPLE | SURFACTANT/ SILICONE in g | GLYCERINE/ SACCHARIN in g | FLAVOR (ml) SORBITOL in g | OTHER ADDITIVES in g | FLOSS TYPE | RESULTS |
| 5 | 10.8/7.2 | 0/1. | 3.5/2 | Carrageenan 0.5 (pre-gelled) | Unwaxed nylon | Dusting dramatically improves mouth feel |
| 6 | 15.8/7.2 | 0/1. | 8/2 | Carrageenan 5 powder | Unwaxed nylon | Improves mouth feel |
| 7 | 39.7/16.8 | 0/2.66 | 19.6/4.7 | Carrageenan 1.77 pre gelled plus powder to dry | Unwaxed nylon | Note in loading there was a single pass thru the chamber. Load was 250 mg/25 yd dry to touch. |
| 8 | 39.7/16.8 | —/2.66 | 19.6/4.7 | Carrageenan 1.77 pre gelled plus powder to dry | Oriented polyester 150/68/4 | Load was 2000 mg/25 yd Dry to touch. |

In Examples 9 thru 39 various compositions were loaded into a white nylon unbonded floss constructed from 6 strands of 140 denier × 64 filaments. The loading was done by passing the floss thru a bath of the compositions maintained at about 210° F. The bath is provided with floss fiber spreading means and the floss is passed through the bath at speeds ranging from between about 1 and about 20 ft/sec. Excess composition is removed using dies and squeegee arrangements. The loaded floss was then passed through a chamber charged with various powder substances which are maintained in a fluid state by a circulating charge of air passed through the

TABLE II

| | LOADING COMPOSITION | | | | | |
|---|---|---|---|---|---|---|
| EXAMPLE | SURFACTANT/ SILICONE in g | GLYCERINE/ SACCHARIN in g | FLAVOR (ml)/ SORBITOL in g | OTHER ADDITIVES in g | FLOSS TYPE | RESULTS |
| 1 | 2.5/5.5 | 0/.2 | 2/0 | — | Bonded nylon | Useable, slightly oily feel |
| 2 | 25.2/10.6 | 0/1.8 | 5/1 | 0.3 methocel K4M | Bonded nylon | Useable, some separation on standing |
| 3 | 7.2/11.5 | 0/1. | 3.5/14 | 0.1 methocel K4M | Bonded nylon | Useable, too much silicone for optimal cleaning |
| 4 | 10.8/7.2 | 0/1. | 3.5/2 | 0.1 methocel K4M powder | Bonded nylon | Useable, better than (3) |

In Examples 5 thru 8 various compositions were loaded into flosses of various constructions and chemical makeup. The loading was done by passing the floss under tension and across fiber spreading devices, in an agitated bath containing these compositions. The loaded floss was then passed through a chamber charged with carrageenan, wherein the chamber was fitted with rubber plugs with carrageenan, wherein the chamber was fitted with rubber plugs provided with slits which serve to remove excess powder. The loaded chamber. Note, in all these Examples the surfactant used was Pluronic F 127; the coating composition, Dow Corning Silicone 1500, the flavor IFF 101. In these Examples there was no glycerin added. The results are described in Table IV below.

Note: these post added powders can include: dicalcium phosphate, carrageenan, Methocel K4M, silica, sodium pyrophosphate, potassium pyrophosphate and similar powdered substances which can improve the hand and/or feel of the treated floss.

TABLE IV

| | LOADING COMPOSITION | | |
|---|---|---|---|
| SURFACTANT/ | FLAVOR (ml) | | DICALCIUM |

TABLE IV-continued

| EXAMPLE | SILICONE in g. | SACCHARIN in g. | SORBITOL in g. | METHOCEL K4M in g. | CARRAGEENAN in g. | PHOSPHATE in g. |
|---|---|---|---|---|---|---|
| 9 | 40/15 | 2.5 | 19.5/5 | — | 18 | — |
| 10 | 50/15 | 2. | 10/5 | — | 18 | — |
| 11 | 50/15 | 2. | 10/5 | — | 18 | — |
| 12 | 50/15 | 2. | 10/5 | — | 18 | — |
| 13 | 50/15 | 2. | 10/5 | — | 18 | — |
| 14 | 60/10 | 2.5 | 15/10 | — | 2.5 | — |
| 15 | 60/10 | 2.5 | 15/10 | — | 2.5 | — |
| 16 | 60/10 | 2.5 | 15/10 | — | 2.5 | — |
| 17 | 40/15 | 2.0 | 15/15 | 13 | — | — |
| 18 | 50/15 | 2.5 | 10/7.5 | — | — | 15 |
| 19 | 50/15 | 2.5 | 10/7.5 | — | — | 15 |
| 20 | 50/15 | 2.5 | 10/7.5 | — | — | 15 |
| 21 | 50/15 | 2.5 | 10/7.5 | — | — | 15 |
| 22 | 50/20 | 2.5 | 10/0 | — | 17.5 | — |
| 23 | 50/20 | 2.5 | 10/0 | — | 17.5 | — |
| 24 | 50/20 | 2.5 | 10/0 | — | 17.5 | — |
| 25 | 50/20 | 2.5 | 10/0 | — | 17.5 | — |
| 26 | 50/15 | 2. | 10/5 | 18 | — | — |
| 27 | 45/18.5 | 1.8 | 14/4.5 | 16.2 | — | — |
| 28 | 50/20 | 2.5 | 13.75/xylitol 30 | — | — | — |
| 29 | 50/15 | 2. | 10/Lycasin powder 10 | — | 8 | — |
| 30 | 50/15 | 2. | 10/Lycasin powder 10 | — | 8 | — |
| 31 | 45/17.5 | 2.25 | 12.5/7.5 | 6.5 | — | 8.75 |
| 32 | 45/17.5 | 2.25 | 12.5/7.5 | 6.5 | — | 8.75 |
| 33 | 47.2/20 | 2. | 10/3.75 | 12.5 | — | 4.5 |
| 34 | 47.2/20 | 2. | 10/3.75 | 12.5 | — | 4.5 |
| 35 | 50/20 | 2.5 | 10/0 | — | 15 | 15 |
| 36 | 200/80 | 10 | IFF 343 Acid Grape 45/100 | — | — | — |
| 37 | 160/70 | 10 | IFF 343 Acid Grape 45/100 | — | — | Silica 50 |
| 38 | 50/20 | 2.5 | 10 | — | 15 | 15 |
| 39 | 50/20 | 2.5 | 10 | — | 15 | 15 |

| | POWDER TREATMENT | | | |
|---|---|---|---|---|
| EXAMPLE | DICALCIUM PHOSPHATE | CARRAGEENAN | METHOCEL K4M | RESULTS |
| 9 | | | + | |
| 10 | | | + | |
| 11 | | + | | |
| 12 | + | | | |
| 13 | + | + | | |
| 14 | | | + | Each version of this series had useful but different properties. Loads ranged from between about 500 to 700 mg/25 yd. |
| 15 | | | + | |
| 16 | + | | | |
| 17 | | | + | |
| 18 | + | | | |
| 19 | | + | | |
| 20 | | | + | |
| 21 | + | | + | |
| 22 | | | | |
| 23 | | | + | |
| 24 | + | | | |
| 25 | + | + | | |
| 26 | + | + | | Load was 500 mg/25 yd |
| 27 | + | + | | Load was 600 mg/25 yd Good mouth feel |
| 28 | + | + | | Crystals of xylitol formed in finished product, coliquid effect in mouth. |
| 29 | | | | Improved mouth feel |
| 30 | + | + | | Improved mouth feel |
| 31 | | | | Powder improves mouth feel. |
| 32 | + | + | | Powder improves mouth feel. |
| 33 | + | | | Loaded 800 mg/25 yd dicalcium phosphate improves cleaning perception, carrageenan improves mouth feel. |
| 34 | | + | | |

TABLE IV-continued

| | | | | |
|---|---|---|---|---|
| 35 | + | + | | Loaded 800 mg/25 yd Best of this group |
| 36 | | + | Silica instead of methocel | Sorbitol makes product different from #45 and very useful (pH controlled at 3.5 with citrate buffer) |
| 37 | | + | Silica instead of methocel | Addition of silica improves cleaning perception. |
| 38 | + | + | | Propyl gallate (0.05%) and BHA (0.05%) added to stabilize. Flavor improves but yellows on storage at 104° F. |
| 39 | + | + | | Propyl gallate (0.1%) and EDTA (0.2%) added to stabilize Flavor and color stable after 7 months at 104° F. |

Various cleaning and coating compositions suitable for use in the preferred flosses of the present invention are described in illustrative Examples 40 thru 48 in Table V below. All percentages listed are by weight.

Various cleaning and coating compositions suitable for incorporation of various biological active ingredients into the preferred flosses of the present invention are described an illustrative Examples 49 to 57 in Table VI. Unless otherwise indicated all units are in percent by weight.

TABLE V

| EXAMPLE | CLEANER (%) | COATING COMPOSITION (%) | SORBITOL (%) | CARRAGEENAN VISCOSIFIER (%) | DICALCIUM PHOSPHATE DENTAL ABRASIVE (%) | FLAVOR |
|---|---|---|---|---|---|---|
| 40 | PEG Stearate/40 | Silicone glycol/20 | 10 | 10 | 15 | 5 |
| 41 | Sodium lauryl sulfate/20 | Carbowax/10 | 20 | 20 | 20 | 10 |
| 42 | Tween-80/30 | Dodecane/10 | 30 | 10 | 10 | 10 |
| 43 | PEG Stearate/20 | Carbowax/10 | 20 | 15 | 25 | 10 |
| 44 | Sodium lauryl sulfate/25 | Dodecane/15 | 25 | 10 | 15 | 10 |
| 45 | Tween-80/40 | Silicone glycol/10 | 15 | 15 | 13 | 7 |
| 46 | PEG Stearate/15 | Dodecane/5 | 30 | 20 | 10 | 10 |
| 47 | Sodium lauryl sulfate/15 | Silicone glycol/15 | 30 | 15 | 15 | 20 |
| 48 | Tween-80/20 | Carbowax/20 | 20 | 15 | 15 | 10 |

TABLE VI

| | INCORPORATION OF VARIOUS BIOLOGICAL ACTIVES | | | | | | | |
|---|---|---|---|---|---|---|---|---|
| EXAMPLE | SURFACTANT F 127 | SILICONE 1500 | CARRAGEENAN | FLAVOR | SACCHARIN | EDTA/PROPYL GALLATE | POLYOL OR ABRASIVE | BIOLOGICAL ACTIVE |
| 49 | 42.75 | 14.25 | 15 | 10.7 | 2 | 0.2/0.1 | silica (10) | tetra sodium pyrophosphate (5) |
| 50 | 45 | 15 | 15 | 5.0 | 3 | 0.2/0.1 | dicalcium phosphate (15) | menthol (0.1) thymo (0.2) eucalyptol (0.2) boric acid 90.5) methyl salicyate (0.2) |
| 51 | 55.5 | 18.5 | — | 9.0 | 1 | 0.2/0.1 | sorbitol (15) | cetylpyrininium chloride (0.1) |
| 52 | 42.75 | 14.25 | 15 | 10 | 2.4 | 0/0.1 | silica (15) | zinc chloride (0.5) |
| 53 | 42.75 | 14.25 | 10 | 10 | 2.9 | 0/0.1 | silica (10) | strontium chloride (desensitizer) (10) |
| 54 | 42.75 | 14.25 | 15 | 10 | 2.5 | — | dicalcium phosphate (15) | metrinidizol (0.5) |
| 55 | 42.75 | 14.25 | 15 | 10 | 2.8 | — | sorbitol (15) | sanguinarine extract (0.2) |
| 56 | 42.75 | 14.25 | 16 | 9.6 | 2.4 | — | sorbitol (15) | polymyxin B sulfate 1000 units/gram) |
| 57 | 39.5 | 13.0 | 15 | 10 | 2.2 | 0.2/0.1 | silica (15) | potassium nitrate (desensitizer) (5) |

EXAMPLE 58

Newburn et al. reported the effect of flossing with iodine impregnated floss in reducing *S. mutans* at specific interproximal sites. Their floss was unwaxed floss, impregnated with 0.2% iodine plus 2% potassium iodide (KI). The control was unwaxed dental floss.

Specifically, Newburn et al. report that, ". . . although flossing alone reduces proportions of *S. mutans*, only the combination of flossing and iodine is effective in achieving a significant reduction. Still, three iodine treatments were not enough to eliminate *S. mutans* permanently from any site".

Gibbons et al. were able to show the long-term effect of iodine at accessible surfaces, but in their study it had little effect on molar interproximal surfaces. Gibbons et al. applied iodine with a syringe and dental floss for 2 min. vs. Newburn's 10 sec/site. Newburn concluded that there is no difference in the effectiveness of iodine whether it it used dried on the floss or with floss dipped into the iodine solution.

In contrast, when the polyvinyl pyrollidone iodine complex is included in the preparations loaded into the preferred floss for the present invention, the effect on *S. mutans* interproximally is most favorable.

The polyvinyl pyrrolidone iodine complex is a stable, effective antimicrobial with minimal staining that is ideally suited for addition to the preferred floss for the present invention.

The PVPI floss preparation can be formulated in the following manner:
1. The required amount of surfactant is melted in a hot water bath maintained at the lowest temperature possible to produce a smooth melt.
2. The required amount of polyvinyl pyrrolidone-iodine complex is added with vigorous mixing to achieve full dispersion, then immediately.
3. The silicone is mixed in until a thick cream is formed.
4. Step (3) is repeated with molten sorbitol and saccharin.
5. The remaining various solid materials, are then added, reserving the flavor oil until last, to reduce volatilization of the oil.

Suitable iodine complex preparations are illustrated in Table VII.

It will be apparent to one skilled in the art that other forms of iodine can be substituted for the PVPI complex with relative ease. For example, potassium iodine can be incorporated into the molten sorbitol or free iodine can be easily dispersed in the molten surfactant at step (1).

EXAMPLE 59

Langner et al. reported in 1984 on the use of tetracycline in various drug delivery systems such as these developed by Goodson. Weeks in 1980, Ciancio in 1976 and Loesche in 1976 have reviewed the use of tetracycline for the treatment of periodontal diseases.

According to Goodson, bacteria have been found to attach to oral tissue with a remarkable degree of specificity. This attachment appears to be the first step in the colonization process. It is reported that low levels of tetracycline applied topically affects the adhesion of suspected periodontal pathogens.

In shallow periodontal pockets, i.e., those no greater than about 3 mm in depth, local periodontitis conditions of patients should improve with regular use of the tetracycline in the load of the floss. One would expect such treatment to dramatically change the periodontal microflora and to rapidly decrease clinical signs of gingival inflammation. When tetracycline is added to the floss in concentrations ranging from between about 60 $\mu$g/yd to about 10 mg/yd, the pathogenic microflora of infected sites can generally be controlled. Generally, the tetracycline released for each interproximal surface flossed is between about 1 mg and about 10 mg, with total release for all 60 surfaces requiring at least about 64 mg/yd.

See Table VIII below for the formulations suitable for the tetracycline floss.

The tetracycline floss preparation can be formulated in the following manner:
1. The required amount of surfactant is melted in a hot water bath maintained at the lowest temperature possible to produce a smooth melt.
2. The required amount of tetracycline is added with vigorous mixing to achieve full dispersion, then immediately thereafter,
3. the silicone is mixed in until a thick cream is formed.
4. Step (3) is repeated with molten sorbitol and saccharin,
5. and then the remaining various solid materials are smoothly incorporated reserving the flavor oils until last, to reduce volatilization of the oils.

TABLE VII

| Surfactant Pluronic F 127 in % | Coating Substance Silicone 1500 in % | Sorbitol in % | Saccharin in % | Flavor IFF 101 in % | Carrageenan in % | Silica in % | Antioxicants Propyl Gallate in % | Iodine, Iodine salt, or Iodine Complex in % |
|---|---|---|---|---|---|---|---|---|
| 48.4 | 24.3 | 10 | 1.0 | 10.0 | — | 6.0 | 0.3 | 1.0 |
| 45.0 | 22.7 | 15 | 1.0 | 10.0 | — | 6.0 | 0.3 | 1.5 |
| 41.8 | 20.9 | 20 | 1.0 | 10.0 | — | 6.0 | 0.3 | 2.0 |
| 51.7 | 26.0 | 5 | 1.0 | 10.0 | — | 6.0 | 0.3 | 0.5 |
| 39.8 | 19.9 | 30 | — | 10.0 | — | — | 0.3 | 3.0 |

| Surfactant Pluronic F127 in % | Coating Substance Silicone 1500 in % | Sorbitol Solution in % | Acid Saccharin in % | Flavor IFF 101 in % | Carrageenan in % |
|---|---|---|---|---|---|
| 48.4 | 24.3 | 10 | 1.0 | 10.0 | — |
| 45.0 | 22.7 | 15 | 1.0 | 10.0 | — |
| 41.8 | 20.9 | 20 | 1.0 | 10.0 | — |
| 51.7 | 26.0 | 5 | 1.0 | 10.0 | — |
| 39.8 | 19.9 | 30 | — | 10.0 | — |

EXAMPLE 60

When the floss described above is processed in a specific manner, it becomes unexpectedly adaptable to the inclusion of historically unstable stannous fluoride.

In the 1950's, Muhler, Bibby, Jordan and others reported their work with stannous fluoride dentifrices for reducing caries in children. These dentifrices were most successful commercially and are credited with the dramatic reductions in caries in children between the '50's and the present.

Stannous fluoride was replaced by sodium fluoride in about 1980 by most fluoride dentifrice manufacturers because of the stability problems encountered with stannous fluoride dentifrices.

For example, an aqueous solution of $SnF_2$ becomes turbid on standing due to hydrolysis to $Sn(OH)_2$ or oxidation to $SnOF_2$. Stratemann in 1974 described $SnF_2$ instability in aqueous systems.

In addition to the anticaries properties reported for $SnF_2$, there has been extensive research directed to the antimicrobial properties of this substance. Kornman in 1986, Tehranirad in 1980 and Tinanoff et al. from 1979 to 1988, have frequently reported on the antiplaque and gingivitis control properties of topically applied $SnF_2$.

Additionally, Svanberg in 1983, reported on dental floss dipped in a $SnF_2$ solution. Keene et al. in 1977 reported working with $SnF_2$, topically applied to teeth, interproximally with floss. All of these researchers reported interproximal antimicrobial effects using their crude floss delivery systems.

The unexpected stability of stannous fluoride in the preferred floss preparations for the present invention were established using the techniques described by Camosci and Tinanoff, J. Dent. Res., 63: 1121-1125 (1984). The stannous fluoride is solubilized in one or more polyols such as sorbitol and added to the preferred floss preparations in the absence of water. Preferably, the mixing and heating of these $SnF_2$ melt preparations are carried out in the absence of oxygen and in metal vessels (to avoid fluoride reactions with glass).

Suitable chemotherapeutic flosses containing $SnF_2$ prepared in this manner are described in the Examples set forth in Table IX below.

tive, non-motile organisms and low numbers of neutrophils.

Periodontal disease is a term used to collectively designate several specific diseases of the gingiva (gingivitis) and of the tissues supporting the teeth (periodontitis). Organisms which grow in the microenvironment of the periodontal pocket are implied as the cause of these periodontal diseases. As the disease becomes established, major changes occur in this environment. It becomes more anaerobic, populated by Gram-negative, often motile organisms and frequently, intermittently infused with large numbers of neutrophils. The environment becomes perfused by an increasing flow of gingival crevice fluid (GCF), the primary aqueous milieu of the periodontal microenvironment.

Alterations of the gingiva seen with gingivitis are principally those associated with inflammation. Gingiva appear red, swollen and bleed easily. This condition is often associated with large numbers of spirochetes and renders the gum tissue painful to touch or probe, and is frequently associated with halitosis. The most common form of gingivitis is due to accumulation of supragingival bacterial plaque and as such is treatable by the preferred $SnF_2$ floss.

Periodontitis is a destructive form of periodontal disease. This condition results in the loss of bone and collagen support of affected teeth. Periodontitis is the result of local infection by specific microorganisms or groups of microorganisms and as such should be amenable to antibacterial therapy such as treatment with the preferred $SnF_2$ floss.

It has been established that even though $SnF_2$ is effective in killing periodontal microorganisms at concentrations commonly used in mouth rinse preparations; delivery as a mouth rinse is inadequate for the treatment of periodontitis. The rinse does not reach the periodontal pocket nor the interproximal sites of infection.

The release of the $SnF_2$ preparations from the floss of the invention subgingivally and interproximally in combination with the unique mechanical action of the floss of the invention offers a new chemo/mechanical therapy to aid in the treatment of less severe sites of periodontitis. In deep periodontal pockets, i.e., 5 to 10 mm deep, the preferred $SnF_2$ floss has lesser effects since

TABLE IX

| | | | | | | | (percent by weight) | |
| --- | --- | --- | --- | --- | --- | --- | --- | --- |
| Surfactant Pluronic F127 in % | Coating Substance Silicone 1500 in % | Polyol/SnF$_2$ Solution in % | Acid Saccharin in % | Flavor IFF 101 in % | Carrageenan in % | Silica in % | Antioxidants in % | SnF$_2$ Concentration in melt-emulsion in % |
| 68 | 16.8 | Glycerin 3.9 | 1.9 | 9.4 | — | — | — | 0.39 |
| 55.8 | 20.6 | Sorbitol 13.0 | 1.3 | 9.3 | — | — | — | 0.39 |
| 55.8 | 16.8 | Sorbitol 13.0 | 1.3 | 9.2 | — | — | — | 0.78 |
| 65.6 | 24.4 | Sorbitol 10 | — | — | — | — | — | 0.30 |
| 55.3 | 20.6 | Sorbitol 10 | 1.3 | 12.8 | — | — | — | 0.30 |
| 46.6 | 17.4 | Sorbitol 10 | 1.1 | 10.8 | 14.1 | — | — | 0.30 |
| 51.6 | 19.2 | Sorbitol 10 | 1.2 | 12.0 | — | 6.0 | — | 0.30 |
| 57.25 | 19.0 | Sorbitol 10 | 0.75 | 7.5 | — | 5.2 | propyl gallate-0.3 | 0.30 |
| 56.8 | 18.95 | Sorbitol 10 | 0.75 | 7.5 | — | 5.1 | propyl gallate-0.3 EDTA-0.6 | 0.30 |

A healthy gingival architecture is characterized by a sulcus of 1 to 3 mm in depth, as measured between the crown of the tooth and the surrounding gingival tissue. Healthy gingiva appears pink, with a firm, stippled surface, and it does not bleed either by mild provocation or spontaneously, and is not painful. The gingival sulcus of a healthy periodontum has low numbers of principally facultative or microaerophilic, gram-posiinfection in pockets of this depth is inaccessible to flossing and serves as a reservoir for reinfection. When surgery and other treatments are used for these conditions, the $SnF_2$ floss shows promise as a maintenance product.

In addition to the anticaries, gingivitis and periodontal treatments discussed above there are additional antimicrobial treatments for specific conditions that lend themselves to the SnF₂ floss. One application is the pretreatment of patients for whom oral surgical procedures are planned. It has long been recognized that any form of dental therapy which creates a laceration of the gingiva produces transient bacteremia. Therefore it would seem that reduction of intraoral organisms such as S. mutans with the SnF₂ containing floss prior to surgical procedures would be helpful. It is noted that *S. mutans* are also associated with endocarditis.

A second situation in which reduction of bacterial numbers appears to provide therapeutic benefit is the surgical post operative maintenance phase. During this period of wound healing, surgical results should be improved by controlling plaque, *S. mutans*, etc. with the SnF₂ floss.

The stabilized SnF₂ flosses used herein offer a new treatment for plaque control and for gingivitis control. As noted above the alterations of the gingiva seen with gingivitis are principally those associated with inflammation, by specific microorganisms or groups of microorganisms. It has been established that this disease is amenable to antibacterial therapy. However, control of this disease is not so much a problem of killing pathogens as it is of altering local microbial ecology. This control of the microbial ecology is achieved by:

a. regular disruption of the subgingival microflora, and
b. disruption or preferably, removal of the supragingival plaque.

It has been observed that gingivitis is a localized condition that is responsive to treatment with the stabilized SnF₂ floss. The release of stabilized SnF₂ preparations into "localized" inflammations and gingival eruptions delivers higher concentrations of SnF₂ antimicrobial interproximally than achievable with any other SnF₂ products such as rinses, gels, dentifrices, etc. This localized delivery of SnF₂ disrupts the local microbial ecology sufficiently to control the infection. Once disrupted, reorganization of the complex gingivitis ecosystem present at a colonization site requires time. It has been found that repeated disruptions via regular flossing prevents such reorganization and is an effective means of controlling the local microbial ecology including *S. mutans*.

Colonization of tooth surfaces by *S. mutans* is not uniform throughout the mouth but instead is highly localized to specific tooth surfaces. As a result, dental caries activity is not uniformly distributed but tends to develop between the teeth, around the necks of teeth, and in fissures on the occlusal surfaces. Therefore, treatments localized to specific tooth surfaces with the SnF₂ floss are proposed. The resultant efficient delivery of SnF₂ in the preparation released from the floss; coupled with the mechanical cleaning of localized tooth surfaces promises superior anticaries clinical effectiveness.

It seems likely that such localized approaches which could affect individual lesions or individual tooth areas could have widespread applicability. For example:

a. The application of orthodontic appliances creates new areas for dental plaque accumulation and constitutes a serious home care problem. The regular use of SnF₂ floss as part of orthodontic appliance use could reduce the Iatrogenic disease liability of these appliances;
b. Mechanically sound dental fillings are commonly replaced due to deterioration of their margins which allow bacterial access to tooth structure and recurrent decay. *S. mutans* colonization accelerates at interproximal restorations according to Keene et al. (1983). Each replacement enlarges the cavity and thereby structurally weakens the tooth. The regular use of SnF₂ floss could extend the longevity of such fillings and maintain a substantially caries free condition, especially at interproximal restorations; and
c. Radiotherapy patients experience accelerated caries which should be treatable with more frequent flossing with the SnF₂ floss.

In these instances it is convenient to carry the stannous fluoride into the melt-emulsion as a solution in a polyol which:

a. is compatible with the melt emulsion,
b. retains and protects the microbiological active properties of the stannous fluoride,
c. presents the stannous fluoride to interproximal sites in a form that is readily solubilized by the fluids present so that it is available for substantial binding to tooth and gum surfaces.

One preferred polyol for stannous fluoride, glycerine, is described in the literature as a carrier for stannous fluoride for water dilutable stannous fluoride rinses, see Yanke et al. (1982). The use of the glycerine-stannous fluoride solution in the melt emulsion process of the present invention is novel. Sorbitol is the most preferred polyol. Surprisingly, sorbitol forms a third phase, solid, at room temperature in the melt-emulsion while simultaneously improving the mouth-feel and various physical properties of the finished floss.

One skilled in the art, having been taught the polyol-stannous fluoride solution technology combined with the melt-emulsion technology of the present invention can appreciate that various alternatives can be substituted for sorbitol, provided such alternative(s) are insoluble in the bulk of the melt-emulsion and capable of forming a third-phase in said melt-emulsion.

The various stannous fluoride preparations of the invention described in Table X below were prepared as follows:

1. A 10% solution of SnF₂ in glycerine was prepared by heating 90 grams anhydrous glycerine USP to about 100° C., then adding 10 g of finely powdered stannous fluoride USP, manufactured by Ozark, Mahoney, Tulsa, Okla.; using vigorous non-vortex stirring. The temperature of the heating bath was slowly raised until the solution clarified.
2. A 3% solution of stannous fluoride in sorbitol was prepared by heating 97 g of anhydrous sorbitol powder (Rochette) in an oil bath maintained at 160°–170°C. When the melt is clear and free of air bubbles, 3.0 g SnF₂ was added with vigorous, non-vortex stirring until the solution clarified. Stannous fluoride is unstable at elevated temperature in the presence of air, so for optimum results this step is timed to be completed immediately prior to the mixing step described below.
3. Requisite quantities of surfactant and coating substance are heated together in an oil bath controlled at 100°–100° C. As the surfactant melts, the mixture easily emulsifies into a uniform "cream" with moderate stirring.
4. To the surfactant, coating composition melt-emulsion of Step (3) above, the required amount of hot stannous fluoride/polyol solution is added [either one of the solutions of stannous fluoride and polyol described in Steps 1 and 2 above] with moderate stirring at 100°–110° C. until all components blend into a uniform emulsion.

5. The remainder of the ingredients, including solids, are added carefully with adequate mixing to ensure that solid particles are occluded by molten surfactant. Due to the volatility of the various flavor oils that can be used, it may be desirable to cool the mixture slightly while retaining fluidity before adding the flavor oils. Antioxidants are most conveniently dispersed in the flavor oil prior to addition to the molten emulsion. If desired, a portion of the antioxidants can be included in the stannous fluoride/polyol solution and incorporated in the melt-emulsion in this manner. Suitable stannous fluoride formulations can be prepared over a broad range of concentrations by increasing the concentration of stannous fluoride in molten sorbitol to 10%, and following the method described in Step 2 above.

3. Chlorhexidine di-laurate is prepared as follows: Note: the di-laurate salt of chlorhexidine was observed not to be soluble in water while being very soluble in ethanol. It is expected that the long dodecene chain could be expected to influence substantivity and retention in the oral cavity. Controlled release of the free base chlorhexidine is expected which in turn is substantive to the teeth and gums (a primary requirement for the therapeutic effectiveness of the drug).

The di-laurate appears to be soluble in the melt-emulsion of the present invention and can be readily prepared in the following manner:
a. Pluronic F-127 (96 g) are melted at 150° C. and 4.0 g chlorhexidine are dissolved as in (1) above.
b. Pluronic F-127 (96.4 g) are melted at 150° C. and 3.6 g (a slight excess over the two equivalents required)

TABLE X

| Surfactant Pluronic F127 in % | Coating Substance Silicone 1500 in % | Sorbitol Polyol/SnF$_2$ Solution in % | Acid Saccharin in % | Flavor IFF 101 in % | Carrageenan in % | Silica in % | (percent by weight) Antioxidants Propyl Gallate in % | SnF$_2$ Concentration in melt-emulsion in % |
|---|---|---|---|---|---|---|---|---|
| 48.4 | 24.3 | 10 | 1.0 | 10.0 | — | 6.0 | 0.3 | 1.0 |
| 45.0 | 22.7 | 15 | 1.0 | 10.0 | — | 6.0 | 0.3 | 1.5 |
| 41.8 | 20.9 | 20 | 1.0 | 10.0 | — | 6.0 | 0.3 | 2.0 |
| 51.7 | 26.0 | 5 | 1.0 | 10.0 | — | 6.0 | 0.3 | 0.5 |
| 39.8 | 19.9 | 30 | — | 10.0 | — | — | 0.3 | 3.0 |

EXAMPLE 61

Chlorhexidine can be successfully incorporated into various flosses used in the present invention according to Examples set forth in Table XI. It is preferred to carry the chlorhexidine into the melt-emulsion either as the free base or as a salt in a solution or uniform dispersion in a non-ionic surfactant compatible with the preparation. Typically Pluronic F-127 (BASF), is used. However, a broad range of other surfactants previously mentioned for the purposes of the present invention are also suitable.

The various chlorhexidine preparations of the invention described in Table XI below, can be prepared in several ways, for example:
1. Chlorhexidine free base is prepared as follows: Ninety nine grams of Pluronic F-127 is melted in an oil bath maintained at 130°-150° C. One gram chlorhexidine base is dispersed with gentle mixing into the melt and stirred until a faintly opalescent solution is obtained. If greater amounts of chlorhexidine are required in the final formulations, 3% is readily added in the same manner. Up to about 10% is compatible using this procedure.
2. Chlorhexidine dilactate is prepared as follows: A more readily water-soluble version of the active ingredient can be compounded by melting 194.2 grams of Pluronic F-127 at 150° C. and dispersing 4.0 g chlorhexidine as in (1) above. A commercial version of Chlorhexidine Lactic Acid (88%) (Chemical Dynamics Corp., South Plainfield, N.J.) is used to provide a slight excess over the two equivalent weights required. Thus, 1.8 g of the specified lactic acid is dispersed into the Pluronic-chlorhexidine solutions above. The resulting dilactate has greater solubility than the free base chlorhexidine described in 1 above and the opalescent character noted previously clears as the reaction proceeds.

of Lauric Acid 95% (Chem. Dynamics Corp., South Plainfield, N.J.) is mixed until dissolved.
c. The prior mixtures (a) and (b) are mixed thoroughly while holding at 150° C.
4. Chlorhexidine di-gluconate is prepared as follows: Note, this water soluble di-gluconate salt of chlorhexidine is the form of choice for a number of therapeutic antimicrobials, including Peridex (TM) (Procter and Gamble) regularly prescribed in a 0.12% concentration mouth rinse for the treatment of gingivitis. Typically, these products start with a water solution of chlorhexidine di-gluconate (20%) (ICI). However, to preserve the substantially non-aqueous formulations of the present invention the following procedure is used:

D-glucono-d-lactone (997) (Chem. Dynamics Corp., S. Plainfield, N.J.) is moistened with slightly more than one equivalent of water (3.6 g) and heated at 75° C. in a closed vessel for 15 minutes. The crystalline, cool tasting, slightly sweet lactone is converted to a very acidic, thick syrup of gluconic acid.
a. Pluronic F-127 (96 g) is melted at 150° C.; and mixed with 4 g chlorhexidine as in 3(a) above.
b. The gluconic acid syrup described above (3.49 g) is mixed with 96.4 g of the melted Pluronic F-127 at 150° C.; resulting in a moderately opalescent solution.
c. The mixtures (a) and (b) above are then mixed thoroughly together while maintaining the temperature at 150° C. The resulting reaction produces a material much less soluble in the non-ionic surfactant than either of the two staring materials and with continued mixing a thick colloidal emulsions forms, thoroughly dispersed throughout the surfactant.

It will be apparent to one skilled in the art that by following the principles taught here, a wide variety of chlorhexidine compounds can be formed in a non-aqueous environment, suitable for incorporation into the flosses employed in the present invention.

Examples of some of these are included in Table XI.

TABLE XI

| Surfactant Pluronic F127 in % | Coating Substance Silicone 1500 in % | Chlorhexidine compound (1) | Saccharin in % | Flavor IFF 101 in % | Carrageenan in % | Silica in % | Sorbitol in % | Chlorhexidine Concentration in melt-emulsion as free base in % |
|---|---|---|---|---|---|---|---|---|
| 72.0 | 17.3 | free base-20 | 0.7 | 10 | — | — | — | 0.2 |
| 57.2 | 12.4 | free base-20 | 0.4 | 10 | — | — | 20 | 0.2 |
| 65.4 | 15.5 | free base-19 | 0.7 | 9.4 | 4.4 | 4.6 | — | 0.19 |
| 79.0 | 16.7 | free base-20 | 0.7 | 2.6 | 5.0 | 5.0 | — | 0.2 |
| 80.0 | 20.0 | free base-20 | — | — | — | — | — | 0.2 |
| 78.5 | 19.5 | free base-20 | 2.0 | — | — | — | — | 0.2 |
| 65.0 | 15.0 | free base-20 | 2.0 | — | 18.0 | — | — | 0.2 |
| 65.0 | 15.0 | free base-20 | 2.0 | — | 10 | 8 | — | 0.2 |
| 57.5 | 12.5 | free base-20 | 2.0 | — | 14.0 | dicalcium phosphate 14.0 | — | 0.2 |
| 50.0 | 10.0 | free base-20 | 2.0 | 10 | 14.0 | dicalcium phosphate 14.0 | — | 0.2 |
| 71.0 | 17 | d. lactate-10 | 2.0 | — | — | — | 10 | 0.4 |
| 70.0 | 19 | d. lactate-20 | 1.0 | 5.0 | — | 5.0 | — | 0.2 |
| 51.5 | 10.5 | d. laurate-10 | 2.0 | 5.0 | 6.0 | 5.0 | 20 | 0.4 |
| 54.0 | 18 | d. laurate-20 | — | — | 8.0 | — | 20 | 0.2 |
| 65.0 | 15 | d. gluconate-10 | 2.0 | 5.0 | 7.0 | 6.0 | — | 0.4 |
| 55.0 | 15 | d. gluconate-20 | 1.0 | 7.0 | — | 7.0 | 15 | 0.2 |
| 57.5 | 12.5 | d. gluconate-20 | 2.0 | 10.0 | 2.0 | 5.0 | 11 | 0.4 |
| 71.0 | 17 | d. laurate-30 | 2.0 | — | — | — | 10 | 0.4 |
| 78.0 | 16 | d. lactate-20 | 1.0 | — | 5.0 | — | — | 0.3 |
| 65.2 | 11.8 | d. lactate-20 | 1.0 | 7.0 | 5.0 | — | 20 | 0.4 |

(1) In surfactant Pluronic F-127 as per 1-4 above.

EXAMPLE 62

The various sodium fluoride preparations of the invention described in Table XII below may be prepared as follows:

1. A 3% solution of sodium fluoride in sorbitol is prepared by heating 97 grams of anhydrous sorbitol powder (Rochette) in an oil bath maintained at 160°-170° C. When the melt is clear and free of air bubbles, add 3.0 grams NaF$_2$ with vigorous, non-vortex stirring until the solution is clear. For optimum results this step is timed to be completed immediately prior to the mixing step described below.
2. Requisite quantities of surfactant and coating substance are heated together in an oil bath controlled at 100√110° C. As the surfactant melts, the mixture easily emulsifies into a uniform "cream" with moderate stirring.
3. To the surfactant, coating composition melt-emulsion of (3) above the required amount of hot sodium fluoride/sorbitol solution is added (one of the solutions of sodium fluoride and polyol described in 1 and 2 above) with moderate stirring at 100°-110°C. until all components blend into a uniform emulsion.
4. The remainder of the ingredients, including solids, are added carefully with adequate mixing to ensure that solid particles are occluded by molten surfactant. Due to the volatility of the various flavor oils that can be used, it may be desirable to cool the mixture slightly while retaining fluidity before adding the flavor oils. Antioxidants are most conveniently dispersed in the flavor oil prior to addition to the molten emulsion. If desired, a portion of the antioxidants can be included in the sodium fluoride, sorbitol solution and incorporated in the melt-emulsion in this manner.
5. Upon cooling the melt-emulsion can be formed into various shapes suitable for use in the methods of loading dental floss above.

Suitable sodium fluoride formulations can be prepared over a broad range of concentrations by increasing the concentration of sodium fluoride in molten sorbitol to 10% following the method described in Step 1 above.

One skilled in the art, having been taught the sorbitol-sodium fluoride solution technology combined with the melt-emulsion technology of the present invention can appreciate that various polyols or other alternatives can be substituted for sorbitol provided such alternative(s) are insoluble in the bulk of the melt-emulsion and capable of forming a third-phase in said melt-emulsion.

TABLE XII

| Surfactant Pluronic F127 in % | Coating Substance Silicone 1500 in % | Sorbitol NaF$_2$ Solution in % | Saccharin in % | Flavor IFF 101 in % | Carrageenan in % | Silica in % | Antioxidants Propyl Gallate in % | NaF$_2$ Concentration in melt-emulsion in % |
|---|---|---|---|---|---|---|---|---|
| 48.4 | 24.3 | 10 | 1.0 | 10.0 | — | 6.0 | 0.3 | 1.0 |
| 45.0 | 22.7 | 15 | 1.0 | 10.0 | — | 6.0 | 0.3 | 1.5 |
| 41.8 | 20.9 | 20 | 1.0 | 10.0 | — | 6.0 | 0.3 | 2.0 |
| 51.7 | 26.0 | 5 | 1.0 | 10.0 | — | 6.0 | 0.3 | 0.5 |
| 39.8 | 19.9 | 30 | — | 10.0 | — | — | 0.3 | 3.0 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of treating the oral cavity to alter local microbial ecology including: plaque formation, gingivitis and S. mutans count comprising treating the oral cavity with an interproximal delivery system comprising:

a) dental floss having from between two and 12 strands, each containing between about 1000 and 800 filaments with a denier between 300 and about 1200, and
b) a cleaning preparation at from between 5 and about 100% by weight of said strands, wherein:
  i. said filaments are substantially free from wax, sizing and binding agents;
  ii. said interproximal delivery system splays upon being worked between interproximal surfaces;
  iii. said interproximal delivery system release from between about 10 and about 80% by weight of said cleaning preparation upon splaying; and
  iv. said cleaning preparation;
    a) is loaded into said delivery system as a substantially aqueous free, hot-melt emulsion,
    b) is contained throughout the interproximal delivery system, primarily in the area surrounding said filaments with less than about 5% by weight of said cleaning preparation on the outermost surface of said delivery system, and
    c) can contain up to about 50% by weight of an active chemotherapeutic agent selected from the group consisting of: antimicrobials, antibiotics, antioxidants, desensitizers, and anti-tartar agents;

wherein the cleaning preparation comprises:
  a. a surfactant selected from the group consisting of:
    sodium lauryl sulfate,
    sodium lauroyl sarcosinate,
    polyethylene glycol stearate,
    polyethylene glycol monostearate,
    coconut monoglyceride sulfonates,
    sodium alkyl sulfate,
    sodium alkyl sulfoacetates,
    block copolymers of polyoxyethylene and polyoxybutylene,
    allylpolyglycol ether carboxylates,
    polyethylene derivatives of sorbitan esters,
    propoxylated cetyl alcohol,
    block copolymers comprising a cogeneric mixture of conjugated polyoxybutylene and polyoxylethylene compound having as a hydrophobe a polyoxybutylene polymer of at least 1200 molecular weight,
    soap powder,
    and mixtures thereof, and
  b. a coating substance insoluble in said surfactant selected from the group consisting of:
    silicones,
    silicone glycol copolymers, and polydimethylsiloxane.

2. A method of releasing interproximally, supragingivally and subgingivally a chemotherapeutic preparation from a dental floss containing an ingestible, oral hygiene cleaning preparation comprising:
  a. a surfactant selected from the group consisting of:
    sodium lauryl sulfate,
    sodium lauroyl sarcosinate,
    polyethylene glycol stearate,
    polyethylene glycol monostearate,
    coconut monoglyceride sulfonates,
    sodium alkyl sulfate,
    sodium alkyl sulfoacetates,
    block copolymers of polyoxyethylene and polyoxybutylene,
    allylpolyglycol ether carboxylates,
    polyethylene derivatives of sorbitan esters,
    propoxylated cetyl alcohol,
    block copolymers comprising a cogeneric mixture of conjugated polyoxybutylene and polyoxylethylene compound having as a hydrophobe a polyoxybutylene polymer of at least 1200 molecular weight,
    soap powder,
    and mixtures thereof; and
  b. a coating substance insoluble in said surfactant selected from the group consisting of:
    silicones,
    silicone glycol copolymers,
    polydimethyl siloxane, and
  c. a chemotherapeutic agent selected from the group consisting of antimicrobials, antibiotics, antioxidants, desensitizers and anti-tartar agents, at a concentration from between about 0.5% and about 3.0% by weight of said preparation;
  wherein said dental floss is substantially free of sizing, binders, and/or wax, and the additives thereon are loaded from a substantially aqueous-free hot melt emulsion;
  and wherein said dental floss is loaded with an amount of readily saliva solubilized surfactant effective to produce a detersive effect in the interproximal region during flowing, said detersive effect being optimized by the conjoint use of the coating substance in the surfactant to avoid foaming, said combination of coating substance and surfactant, when presented interproximally, producing surface active properties effective to assist cleaning of debris and plaque from the interproximal sites, to condition teeth and gums, to alter the surface tension of the plaque as well as disrupt plaque reattachment.

3. The method of claim 1, wherein the floss further contains a powder substance separate from said preparation selected from the group consisting of abrasives, gums, viscosity control agents, polyols and mixtures thereof.

4. The method of claim 1, wherein the cleaning preparation is loaded into the floss at a rate between about 20 and about 50 mg/yd and wherein said preparation releases at a rate between about 30% and about 70% by weight of the load.

5. The method of claim 1, wherein the cleaning preparation is loaded into the floss at a rate between about 10 mg/yd and about 100 mg/yd.

6. The method of claim 1, wherein the cleaning preparation contains an abrasive selected from the group consisting of silica, calcium carbonate, talc, dicalcium phosphate and mixtures thereof.

7. The method of claim 1, wherein the cleaning preparation contains a desensitizer.

8. The method of claim 1, wherein the cleaning preparation contains an anti-oxidant.

9. A method of treating dental fillings including interproximal restorations, which comprises flossing with a dental floss containing an ingestible, oral hygiene cleaning preparation containing an active chemotherapeutic agent, said cleaning preparation comprising:
  a. a surfactant selected from the group consisting of:
    sodium lauryl sulfate,
    sodium lauroyl sarcosinate,
    polyethylene glycol stearate,
    polyethylene glycol monostearate,
    coconut monoglyceride sulfonates,
    sodium alkyl sulfate, sodium alkyl sulfoacetates,
block copolymers of polyoxyethylene and polyoxybutylene,
allylpolyglycol ether carboxylates,
polyethylene derivatives of sorbitan esters,
propoxylated cetyl alcohol,
block copolymers comprising a cogeneric mixture of conjugated polyoxybutylene and polyoxylethylene compound having as a hydrophobe a polyoxybutylene polymer of at least 1200 molecular weight,
soap powder,
and mixtures thereof; and b. a coating substance insoluble in said surfactant selected from the group consisting of:
silicones,
silicones glycol copolymers,
polydimethyl siloxane, and c. an active chemotherapeutic agent selected from the group consisting of tetracycline, chlorhexidine, stannous fluoride, sodium fluoride, and polyvinyl pyrrolidone iodine complex (PVPI), at a concentration from between about 0.5% to about 10.0% by weight of said preparation;

wherein said dental floss is substantially free of sizing, binders, and/or wax, and the additives thereon are loaded from a substantially aqueous-free hot melt emulsion;

and wherein said dental floss is loaded with an amount of readily saliva solubilized surfactant effective to produce a detersive effect in the interproximal region during flossing, said detersive effect being optimized by the conjoint use of the coating substance in the surfactant to avoid foaming, said combination of coating substance and surfactant, when presented interproximally, producing surface active properties effective to assist cleaning of debris and plaque from the interproximal sites, to condition teeth and gums, to alter the surface tension of the plaque as well as disrupt plaque reattachment.

10. A method of treating caries in radiotherapy patients comprising flossing with a dental floss containing an ingestible, oral hygiene cleaning preparation containing an active chemotherapeutic agent, said cleaning preparation comprising:

a. a surfactant selected from the group consisting of:
sodium lauryl sulfate,
sodium lauroyl sarcosinate,
polyethylene glycol stearate,
polyethylene glycol monostearate,
coconut monoglyceride sulfonates,
sodium alkyl sulfate,
sodium alkyl sulfoacetates,
block copolymers of polyoxyethylene and polyoxybutylene,
allylpolyglycol ether carboxylates,
polyethylene derivatives of sorbitan esters,
propoxylated cetyl alcohol,
block copolymers comprising a cogeneric mixture of conjugated polyoxybutylene and polyoxylethylene compound having as a hydrophobe a polyoxybutylene polymer of at least 1200 molecular weight,
soap powder,
and mixtures thereof; and b. a coating substance in soluble in said surfactant selected from the group consisting of:
silicones,
silicone glycol copolymers,
polydimethyl siloxane, and c. an active chemotherapeutic agent selected from the group consisting of tetracycline, chlorhexidine, stannous fluoride, sodium fluoride, and polyvinyl pyrrolidone iodine complex (PVPI), at a concentration from between about 0.55 to about 10.0% by weight of said preparation;

wherein said dental floss is substantially free of sizing, binders, and/or wax, and the additives thereon are loaded from a substantially aqueous-free hot melt emulsion;

and wherein said dental floss is loaded with an amount of readily saliva solubilized surfactant effective to produce a detersive effect in the interproximal region during flossing said detersive effect being optimized by the conjoint use of the coating substance in the surfactant to avoid foaming, said combination of coating substance and surfactant, when presented interproximally, producing surface active properties effective to assist cleaning of debris and plaque from the interproximal sites, to condition teeth and gums, to alter the surface tension of the plaque as well as disrupt plaque reattachment.

11. A method of treating periodontitis comprising flossing with a dental floss containing an ingestible, oral hygiene cleaning preparation containing an active chemotherapeutic agent, said cleaning preparation comprising:

a. a surfactant selected from the group consisting of:
sodium lauryl sulfate,
sodium lauroyl sarcosinate,
polyethylene glycol stearate,
polyethylene glycol monostearate,
coconut monoglyceride sulfonates,
sodium alkyl sulfate,
sodium alkyl sulfoacetates,
block copolymers of polyoxyethylene and polyoxybutylene,
allylpolyglycol ether carboxylates,
polyethylene derivatives of sorbitan esters,
propoxylated cetyl alcohol,
block copolymers comprising a cogeneric mixture of conjugated polyoxybutylene and polyoxyethylene compound having as a hydrophobe a polyoxybutylene polymer of at least 1200 molecular weight,
soap powder,
and mixtures thereof; and b. a coating substance insoluble in said surfactant selected from the group consisting of:
silicones;
silicone glycol copolymers,
polydimethyl siloxane, and c. an active chemotherapeutic agent selected from the group consisting of tetracycline, chlorhexidine, stannous fluoride, sodium fluoride, and polyvinyl pyrrolidone iodine complex (PVPI), at a concentration from between about 0.5% to about 10.0% by weight of said preparation;

wherein said dental floss is substantially free of sizing, binders, and/or wax, and the additives thereon are loaded from a substantially aqueous-free hot melt emulsion;

and wherein said dental floss is loaded with an amount of readily saliva solubilized surfactant effective to produce a detersive effect in the interproximal region during flossing, said detersive effect being optimized by the conjoint use of the coating substance in the surfactant to avoid foaming, said combination of coating substance and surfactant, when presented interproximally, producing surface active properties effective to assist cleaning of debris and plaque from the interproximal sites, to condition teeth and gums, to alter the surface tension of the plaque as well as disrupt plaque reattachment.

12. A method of pretreating oral surgery patients comprising flossing prior to surgery with a dental floss containing an ingestible, oral hygiene cleaning preparation containing an active chemotherapeutic agent, said cleaning preparation comprising:
   a. a surfactant selected from the group consisting of:
      sodium lauryl sulfate,
      sodium lauroyl sarcosinate,
      polyethylene glycol stearate,
      polyethylene glycol monostearate,
      coconut monoglyceride sulfonates,
      sodium alkyl sulfate,
      sodium allyl sulfoacetates,
      block copolymers of polyoxyethylene and polyoxybutylene,
      allylpolyglycol ether carboxylates,
      polyethylene derivatives of sorbitan esters,
      propoxylated cetyl alcohol,
      block copolymers comprising a cogeneric mixture of conjugated polyoxybutylene and polyoxylethylene compound having as a hydrophobe a polyoxybutylene polymer of at least 1200 molecular weight,
      soap powder,
      and mixtures thereof; and
   b. a coating substance insoluble in said surfactant selected from the group consisting of:
      silicones,
      silicone glycol copolymers,
      polydimethyl siloxane, and
   c. an active chemotherapeutic agent selected from the group consisting of tetracycline, chlorhexidine, stannous fluoride, sodium fluoride, and polyvinyl pyrrolidone iodine complex (PVPI), at a concentration from between about 0.5% to about 10.0% by weight of said preparation;
   wherein said dental floss is substantially free of sizing, binders, and/or wax, and the additives thereon are loaded from a substantially aqueous-free hot melt emulsion;
   and wherein said dental floss is loaded with an amount of readily saliva solubilized surfactant effective to produce a detersive effect in the interproximal region during flossing, said detersive effect being optimized by the conjoint use of the coating substance in the surfactant to avoid foaming, said combination of coating substance and surfactant, when presented interproximally, producing surface active properties effective to assist cleaning of debris and plaque from the interproximal sites, to condition teeth and gums, to alter the surface tension of the plaque as well as disrupt plaque reattachment.

13. A method of post-treating oral surgery patients comprising flossing after surgery with a dental floss containing an ingestible, oral hygiene cleaning preparation containing an active chemotherapeutic agent, said cleaning preparation comprising:
   a. a surfactant selected from the group consisting of:
      sodium lauryl sulfate,
      sodium lauroyl sarcosinate,
      polyethylene glycol stearate,
      polyethylene glycol monostearate,
      coconut monoglyceride sulfonates,
      sodium alkyl sulfate,
      sodium alkyl sulfoacetates,
      block copolymers of polyoxyethylene and polyoxybutylene,
      allylpolyglycol ether carboxylates,
      polyethylene derivatives of sorbitan esters,
      propoxylated cetyl alcohol,
      block copolymers comprising a cogeneric mixture of conjugated polyoxybutylene and polyoxylethylene compound having as a hydrophobe a polyoxybutylene polymer of at least 1200 molecular weight,
      soap powder,
      and mixtures thereof; and
   b. a coating substance insoluble in said surfactant selected from the group consisting of:
      silicones,
      silicone glycol copolymers,
      polydimethyl siloxane, and
   c. an active chemotherapeutic agent selected from the group consisting of tetracycline, chlorhexidine, stannous fluoride, sodium fluoride, and polyvinyl pyrrolidone iodine complex (PVPI), at a concentration from between about 0.5% to about 10.0% by weight of said preparation;
   wherein said dental floss is substantially free of sizing, binders, and/or wax, and the additives thereon are loaded from a substantially aqueous-free hot melt emulsion;
   and wherein said dental floss is loaded with an amount of readily saliva solubilized surfactant effective to produce a detersive effect in the interproximal region during flossing, said detersive effect being optimized by the conjoint use of the coating substance in the surfactant to avoid foaming, said combination of coating substance and surfactant, when presented interproximally, producing surface active properties effective to assist cleaning of debris and plaque from the interproximal sites, to condition teeth and gums, to alter the surface tension of the plaque as well as disrupt plaque reattachment.

* * * * *